United States Patent
Bhamidipati et al.

(10) Patent No.: US 8,268,851 B2
(45) Date of Patent: Sep. 18, 2012

(54) COMPOSITIONS AND METHODS FOR INHIBITION OF THE JAK PATHWAY

(75) Inventors: Somasekhar Bhamidipati, Foster City, CA (US); Hui Li, Santa Clara, CA (US); Rajinder Singh, Belmont, CA (US); Vanessa Taylor, San Francisco, CA (US); Jeffrey Clough, Redwood City, CA (US); Darren McMurtrie, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 220 days.

(21) Appl. No.: 12/645,349

(22) Filed: Dec. 22, 2009

(65) Prior Publication Data

US 2010/0158921 A1 Jun. 24, 2010

Related U.S. Application Data

(60) Provisional application No. 61/140,604, filed on Dec. 23, 2008.

(51) Int. Cl.
*A01N 43/54* (2006.01)
*A61K 31/505* (2006.01)

(52) U.S. Cl. ........................................ 514/275; 544/323

(58) Field of Classification Search .................... 544/323
See application file for complete search history.

(56) References Cited

FOREIGN PATENT DOCUMENTS

| WO | WO2008079907 A1 | 7/2008 |
| WO | WO 2008118822 A1 * | 10/2008 |
| WO | WO2008118822 A1 | 10/2008 |
| WO | WO2008118823 A2 | 10/2008 |
| WO | WO2010075558 A3 | 7/2010 |

OTHER PUBLICATIONS

The Condensed Chemical Dictionary 822 (Gessner G. Hawley ed., 9th ed., 1977); Concise Chemical and Technical Dictionary 1081 (H. Bennett ed., 4th ed., 1986); Hawley's Condensed Chemical Dictionary 1186 (Richard J. Lewis, Sr. ed., 15th ed., 2007).*
J.H. Poupaert, Drug Design: Basic Principles and Applications, in 2 Encyclopedia of Pharmaceutical Technology 1362-1369, 1367 (James Swarbrick ed., 3rd ed., 2007).*
L.I. Zon et al., Nature Reviews Drug Discovery 4, 35 (2005).*
Veljikovic et al., Current Medicinal Chemistry, 14, 441-443 (2007).*

* cited by examiner

*Primary Examiner* — James O Wilson
*Assistant Examiner* — Alexander R Pagano
(74) *Attorney, Agent, or Firm* — Klarquist Sparkman, LLP

(57) ABSTRACT

The invention encompasses compounds having formula I and the compositions and methods using these compounds in the treatment of conditions in which modulation of the JAK pathway or inhibition of JAK kinases, particularly JAK3, are therapeutically useful.

14 Claims, No Drawings

COMPOSITIONS AND METHODS FOR INHIBITION OF THE JAK PATHWAY

CROSS REFERENCE TO RELATED APPLICATIONS

This application claims the benefit of the earlier filing date of U.S. provisional application Ser. No. 61/140,604, filed Dec. 23, 2008.

I. INTRODUCTION

A. Field

The present invention relates to compounds, prodrugs, and methods of using these compounds and prodrugs thereof in the treatment of conditions in which modulation of the JAK pathway or inhibition of JAK kinases, particularly JAK3, are therapeutically useful.

B. Background

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor—mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). JAK3 kinases have also been implicated in the mechanism involved in early and late stages of rheumatoid arthritis (Muller-Ladner et al., (2000), *J. Immunal.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine compounds for use in the treatment of conditions in which targeting of the JAK pathway or inhibition of JAK kinases, particularly JAK3, are therapeutically useful.

II. SUMMARY

The invention is directed to compounds, prodrugs, pharmaceutical compositions and methods of using them in the treatment of conditions in which modulation of the JAK pathway or inhibition of JAK kinases, particularly JAK3, will be therapeutically useful.

In one embodiment, this invention provides a compound of formula I:

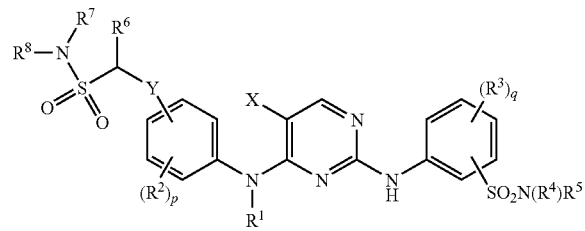

wherein:
p is 0, 1, 2, or 3;
q is 0, 1, 2, or 3;
X is hydrogen, alkyl, substituted alkyl, hydroxy, alkoxy, substituted alkoxy, amino, substituted amino, carboxyl, carboxyl ester, —C(O)N(R$^4$)R$^5$, cyano, halo, nitro, alkenyl, substituted alkenyl, alkynyl, substituted alkynyl, cycloalkynyl or substituted cycloalkynyl;
Y is a straight or branched chain C$_{1-6}$ alkylene group, cycloalkylene or substituted cycloalkylene;
R$^1$ is hydrogen, alkyl, substituted alkyl, cycloalkyl or substituted cycloalkyl;
each R$^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N(R$^4$)R$^5$, nitro or halo;
each R$^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;
each R$^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or M$^+$ wherein M$^+$, a counterion, is K$^+$, Na$^+$, Li$^+$ or $^+$N(R$^9$)$_4$, wherein each R$^9$ independently is hydrogen or alkyl, and the nitrogen immediately adjacent to R$^5$ is anionic; or
R$^4$ and R$^5$ together with the intervening atom or atoms bound thereto, form a heterocyclyl or substituted heterocyclyl group;
each R$^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;

R$^6$ is hydrogen, alkyl, substituted alkyl, cycloalkyl, substituted cycloalkyl, heterocyclyl, substituted heterocyclyl, aryl, substituted aryl, heteroaryl, substituted heteroaryl and acyl;
R$^6$ is a straight or branched chain C$_{1-6}$ alkylene group, cycloalkylene or substituted cycloalkylene, linking the nitrogen bearing R$^6$ and the ring bearing Y
R$^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
R$^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
optionally, R$^7$ and R$^8$, together with nitrogen to which they are bound, form a heterocyclyl or substituted heterocyclyl group;
wherein at least one of R$^7$ and R$^8$ is non-hydrogen; and
each of R$^6$, R$^7$, and R$^8$ optionally are M$^+$ wherein M$^+$, a counter-ion, is K$^+$, Na$^+$, Li$^+$ or $^+$N(R$^9$)$_4$, wherein each R$^9$ independently is hydrogen or alkyl, and the nitrogen bearing M$^+$ is anionic.

In certain implementations, the invention provides compounds of formula II:

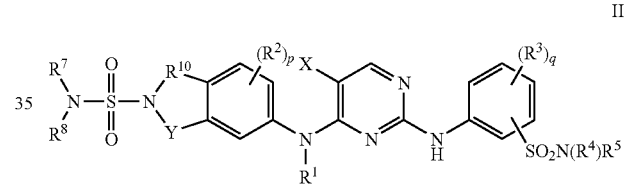

wherein
R$^{10}$ is a straight or branched chain C$_{1-6}$ alkylene group, cycloalkylene or substituted cycloalkylene, and the remaining variables are as defined as for formula I except that included are compounds where R$^7$ and R$^8$ are simultaneously hydrogen.

Yet other implementations of the invention provide compounds of formula III:

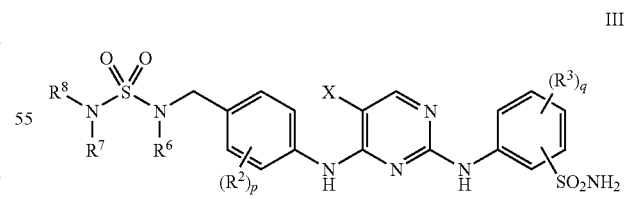

wherein:
X is alkyl, substituted alkyl, hydroxy, alkoxy, substituted alkoxy, amino, substituted amino, carboxyl, carboxyl ester, —C(O)N(R$^4$)R$^5$, cyano, halo, nitro, alkenyl, substituted alkenyl, alkynyl, substituted alkynyl, cycloalkynyl or substituted cycloalkynyl; and the remaining variables are as defined for compounds of formula I.

Another implementation of the invention provides compounds of formula IV:

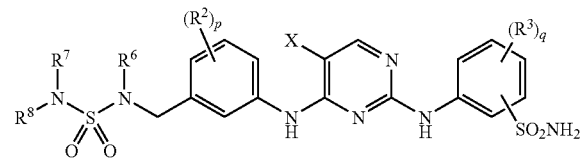

wherein:
X is alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl; and the remaining variables are as defined for compounds of formula I.

Another embodiment is a method of inhibiting an activity of a JAK kinase, including contacting the JAK kinase with an amount of a compound effective to inhibit an activity of the JAK kinase where the compound is according to formula I as described herein. In one embodiment the contact is made in vitro, in another embodiment the contact is made in vivo.

Another embodiment is a method of treating a T-cell mediated autoimmune disease, including administering to a patient suffering from such an autoimmune disease an amount of a compound effective to treat the autoimmune disease where the compound is according to formula I as described herein.

Another embodiment is a method of treating or preventing allograft transplant rejection in a transplant recipient, including administering to the transplant recipient an amount of a compound effective to treat or prevent the rejection where the compound is according to formula I as described herein. Administration in this context may include contacting a transplant organ with a compound or pharmaceutical composition described herein prior to transplant and/or concurrent with administration to the transplant recipient.

Yet another embodiment is a method of treating or preventing a Type IV hypersensitivity reaction, including administering to a subject an amount of a compound of effective to treat or prevent the hypersensitivity reaction where the compound is according to formula I as described herein.

Another embodiment is a method of treating or preventing an ocular disease or disorder, including administering to a subject an amount of a compound of effective to treat or prevent the ocular disease or disorder where the compound is according to formula I as described herein.

Another embodiment is a method of inhibiting a signal transduction cascade in which JAK3 kinase plays a role, including contacting a cell expressing a receptor involved in such a signaling cascade with a compound where the compound is according to formula I as described herein.

Another embodiment is a method of treating or preventing a JAK kinase-mediated disease, including administering to a subject an amount of compound effective to treat or prevent the JAK kinase-mediated disease where the compound is according to formula I as described herein.

Another embodiment is a pharmaceutical formulation including a compound of formula I as described herein. Therapy using the 2,4-pyrimidinediamine compounds and pharmaceutical formulations described herein can be applied alone, or it can be applied in combination with or adjunctive to other common immunosuppressive therapies Other embodiments include methods of using the compounds for screening for other agents used to treat or prevent a JAK kinase mediated disease.

More detailed description for these and other embodiments is provided below.

III. DETAILED DESCRIPTION

A. Overview

The invention encompasses compounds having formula I and the compositions and methods using these compounds in the treatment of conditions in which modulation of the JAK pathway or inhibition of JAK kinases, particularly JAK3, are therapeutically useful.

B. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. Acyl includes the "acetyl" group $CH_3C(O)$—.

"Acylamino" refers to the groups $NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclyl, and —$NR^{20}C(O)$substituted heterocyclyl, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclyl-C(O)O—, and substituted heterocyclyl-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amino" refers to the group —NH$_2$.

"Aminocarbonyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Aminothiocarbonyl" refers to the group —C(S)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, awl, substituted aryl, heteroaryl, substituted heteroaryl, heterocyclyl, and substituted heterocyclyl are as defined herein.

"Aminocarbonylamino" refers to the group —NR$^{20}$C(O)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminothiocarbonylamino" refers to the group —NR$^{20}$C(S)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted awl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminocarbonyloxy" refers to the group —O—C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted awl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, awl, substituted aryl, heteroaryl, substituted heteroaryl, heterocyclyl and substituted heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl and where R$^{21}$ and R$^{22}$ are optionally joined together with the nitrogen bound thereto to form a heterocyclyl or substituted heterocyclyl group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein.

"Aminosulfonyloxy" refers to the group —O—SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl; R$^{21}$ and R$^{22}$ are optionally joined together with the nitrogen bound thereto to form a heterocyclyl or substituted heterocyclyl group; and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Aminosulfonylamino" refers to the group —NR$^{20}$—SO$_2$NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the nitrogen bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, awl, substituted aryl, heteroaryl, substituted heteroaryl, heterocyclyl and substituted heterocyclyl are as defined herein.

"Sulfonylamino" refers to group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{21}$ and R$^{22}$ are optionally joined together with the atoms bound thereto to form a heterocyclyl or substituted heterocyclyl group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amidino" refers to the group —C(=NR$^{30}$)NR$^{31}$R$^{32}$, wherein R$^{31}$ and R$^{32}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{31}$ and R$^{32}$ are optionally joined together with the nitrogen bound thereto to form a heterocyclyl or substituted heterocyclyl group. R$^{30}$ is selected from the group consisting of hydrogen, alkyl, substituted alkyl, alkenyl, substituted alkenyl, alkynyl, substituted alkynyl, cycloalkynyl, substituted cycloalkynyl, aryl, substituted aryl, cycloalkyl, substituted cycloalkyl, cycloalkenyl, substituted cycloalkenyl, heteroaryl, substituted heteroaryl, heterocyclyl, substituted heterocyclyl, nitro, nitroso, hydroxy, alkoxy, cyano, —N=N—N-alkyl, —N=N—N-substituted alkyl, —N(alkyl)SO$_2$-alkyl, —N(alkyl)SO$_2$-substituted alkyl, —N=N=N-alkyl, —N=N=N— substituted alkyl, acyl, —SO$_2$-alkyl and —SO$_2$-substituted alkyl, wherein alkyl, substituted alkyl, alkenyl, substituted alkenyl, alkynyl, substituted alkynyl, cycloalkynyl, substituted cycloalkynyl, cycloalkyl, substituted cycloalkyl, cycloalkenyl, substituted cycloalkenyl, aryl, substituted aryl, heteroaryl, substituted heteroaryl, heterocyclyl, substituted heterocyclyl, nitro, nitroso, hydroxy, alkoxy, and cyano are as defined herein. One of R$^{31}$ and R$^{32}$ along with R$^{30}$ are optionally joined together with the nitrogens bound thereto and the intervening carbon of the guanidine group to form a cyclic amidine.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like), provided that the point of attachment is through an atom of the aromatic aryl group. Preferred aryl groups include phenyl and naphthyl.

"Aryloxy" refers to the group —O-aryl, wherein awl is as defined herein, including, by way of example, phenoxy, naphthoxy, and the like.

"Arylthio" refers to the group —S-aryl, wherein aryl is as defined herein. In other embodiments, sulfur may be oxidized to —S(O)— or —SO$_2$— moieties. Depending on the pendant substitution, the sulfoxide may impart chirality to the molecule.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. Such groups are exemplified, for example, bi-vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

"Alkynyloxy" refers to the group —O-alkynyl, wherein alkynyl is as defined herein. Alkynyloxy includes, by way of example, ethynyloxy, propynyloxy, and the like.

"Carboxyl," "carboxy" or "carboxylate" refers to —CO$_2$H or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclyl, and —C(O)O-substituted heterocyclyl, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted awl, heteroaryl, substituted heteroaryl, heterocyclyl, and substituted heterocyclyl are as defined herein.

"(Carboxyl ester)amino" refers to the groups —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclyl, and —NR—C(O)O-substituted heterocyclyl, wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclyl, and —O—C(O)O-substituted heterocyclyl, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 5 to 10 carbon atoms having single or multiple rings and having at least one triple bond.

"Cycloalkylene" refers to divalent cycloalkyl groups, wherein cycloalkyl is as defined herein.

"Cycloalkoxy" refers to —O-cycloalkyl.

"Cycloalkylthio" refers to —S-cycloalkyl. In other embodiments, sulfur may be oxidized to —S(O)— or —SO$_2$— moieties. Depending on the pendant substitution, the sulfoxide may impart chirality to the molecule.

"Cycloalkenyloxy" refers to ±0-cycloalkenyl.

"Cycloalkenylthio" refers to —S-cycloalkenyl. In other embodiments, sulfur may be oxidized to sulfinyl or sulfonyl moieties. Depending on the pendant substitution, the sulfoxide may impart chirality to the molecule.

"Guanidino" refers to the group —NHC(=NH)NH$_2$.

"Substituted guanidino" refers to the group —NR$^{33}$C(=NR$^{33}$)N(R$^{33}$)$_2$, wherein each R$^{33}$ independently is selected from the group consisting of hydrogen, alkyl, substituted alkyl, aryl, substituted awl, heteroaryl, substituted heteroaryl, heterocyclyl, and substituted heterocyclyl; two R groups attached to a common guanidino nitrogen atom are optionally joined together with the nitrogen bound thereto to form a heterocyclyl or substituted heterocyclyl group, provided that at least one R is not hydrogen; and said substituents are as defined herein. Two R$^{33}$ groups on distinct nitrogens are optionally joined together with the nitrogens bound thereto and the intervening carbon of the guanidine group to form a cyclic guanidine.

"Halo" or "halogen" refers to fluoro, chloro, bromo, and iodo and is preferably fluoro or chloro.

"Hydroxy" or "hydroxyl" refers to the group —OH.

"Heteroaryloxy" refers to —O-heteroaryl.

"Heteroarylthio" refers to the group —S-heteroaryl. In other embodiments, sulfur may be oxidized to —S(O)— or —SO$_2$— moieties. The sulfoxide may exist as one or more stereoisomers.

"Heterocyclyl" in the broadest sense includes aromatic and non-aromatic ring systems and more specifically refers to a stable three- to fifteen-membered ring radical that consists of carbon atoms and from one to five heteroatoms. For purposes of this invention, the heterocyclyl radical can be a monocyclic, bicyclic or tricyclic ring system, which can include fused or bridged ring systems as well as spirocyclic systems; and the nitrogen, phosphorus, carbon or sulfur atoms in the heterocyclyl radical can be optionally oxidized to various oxidation states. In a specific example, the group —S(O)$_{0-2}$—, refers to —S-(sulfide), —S(O)— (sulfoxide), and —SO$_2$— (sulfone) linkages. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is meant to be included as another compound of the invention. In addition, annular nitrogen atoms can be optionally quaternized. "Heterocycle" includes heteroaryl and heteroalicyclyl, that is a heterocyclyl ring can be partially or fully saturated or aromatic. Thus a term such as "heterocyclylalkyl" includes heteroalicyclylalkyls and heteroarylalkyls. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroaryl" refers to an aromatic group of having from 1 to 10 annular carbon atoms and 1 to 4 annular heteroatoms within the ring. Heteroaryl groups have at least one aromatic ring component, but heteroaryls can be fully unsaturated or partially unsaturated. If any aromatic ring in the group has a heteroatom, then the group is a heteroaryl, even, for example, if other aromatic rings in the group have no heteroatoms. For example, 2H-pyrido[3,2-b][1,4]oxazin-3(4H)-one-7-yl, indolyl and benzimidazolyl are "heteroaryls." Heteroaryl groups can have a single ring (e.g., pyridinyl, imidazolyl or furyl) or multiple condensed rings (e.g., indolizinyl, quinolinyl, benzimidazolyl or benzothienyl), where the condensed rings may or may not be aromatic and/or contain a heteroatom, provided that the point of attachment to the parent molecule is through an atom of the aromatic portion of the heteroaryl group. In one embodiment, the nitrogen and/or sulfur ring atom(s) of the heteroaryl group are optionally oxidized to provide for the N-oxide (N→O), sulfinyl, or sulfonyl moieties. Compounds described herein containing phosphorous, in a heterocyclyl ring or not, include the oxidized forms of phosphorous. Heteroaryl groups are monocyclic, bicyclic, tricyclic or tetracyclic, and the like.

"Heteroaryloxy" refers to —O-heteroaryl.

"Heteroarylene" generically refers to any heteroaryl that has at least two groups attached thereto. For a more specific example, "pyridylene" refers to a divalent pyridyl ring radical. A pyridylene, thus can have more than two groups attached, but is defined by a minimum of two non-hydrogen groups attached thereto.

"Heteroalicyclic" refers specifically to a non-aromatic heterocyclyl radical. A heteroalicyclic may contain unsaturation, but is not aromatic. As mentioned, aryls and heteroaryls are attached to the parent structure via an aromatic ring. So, e.g., 2H-1,4-benzoxazin-3(4H)-one-4-yl is a heteroalicyclic, while 2H-1,4-benzoxazin-3(4H)-one-7-yl is an aryl. In another example, 2H-pyrido[3,2-b][1,4]oxazin-3(4H)-one-4-yl is a heteroalicyclic, while 2H-pyrido[3,2-b][1,4]oxazin-3(4H)-one-7-yl is a heteroaryl.

"Heterocyclylalkyl" refers to a heterocyclyl group linked to the parent structure via e.g an alkylene linker, for example (tetrahydrofuran-3-yl)methyl- or (pyridin-4-yl)methyl

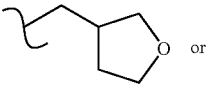 or 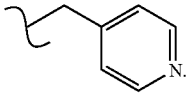

"Heterocyclyloxy" refers to the group —O-heterocycyl.

"Heterocyclylthio" refers to the group —S-heterocycyl. In other embodiments, sulfur may be oxidized to —S(O)— or SO$_2$— moieties. The sulfoxide may exist as one or more stereoisomers.

"Nitro" refers to the group —NO$_2$.

"Nitroso" refers to the group —NO.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cylcoalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclyl, and SO$_2$-substituted heterocyclyl, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. Sulfonyl includes groups such as methyl-SO$_2$—, phenyl-SO$_2$—, and 4-methylphenyl-SO$_2$—.

"Sulfonyloxy" refers to the group OSO$_2$-alkyl, OSO$_2$-substituted alkyl, OSO$_2$-alkenyl, OSO$_2$-substituted alkenyl, OSO$_2$-cycloalkyl, OSO$_2$-substituted cylcoalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclyl, and OSO$_2$ substituted heterocyclyl, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclyl-C(S)—, and substituted heterocyclyl-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Thiol" refers to the group —SH.

"Thioxo" refers to the atom (=S).

"Alkylthio" refers to the group —S-alkyl, wherein alkyl is as defined herein. In other embodiments, sulfur may be oxidized to —S(O)—. The sulfoxide may exist as one or more stereoisomers.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "substituted," when used to modify a specified group or radical, means that one or more hydrogen atoms of the specified group or radical are each, independently of one another, replaced with the same or different substituent groups as defined below.

Substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC (O)R$^{70}$, —OC(S)R$^{70}$, —OC(O) O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, NR$^{70}$C(NR$^{70}$)R$^{70}$ and —NR$^{70}$C (NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, NR$^{80}$R$^{80}$ is meant to include —NH$_2$, —NH-alkyl, N-pyrrolidinyl, N-piperazinyl, 4N-methyl-piperazin-1-yl and N-morpholinyl.

Substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{80}$CO$_2$R$^{70}$, —NR$^{70}$C(S)OR$^{70}$, —NR$^{70}$C(O)NR$^{80}$R$^{80}$, —NR$^{70}$C(NR$^{70}$) R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^-$.

Substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O) (O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC (O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$) R$^{70}$ and —NR$^{80}$C(NR$^{70}$)NR$^{80}$R$^{80}$, where R$^{60}$, R$^{70}$, R$^{80}$ and M$^+$ are as previously defined.

In a preferred embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted awl group as a substituent which is itself substituted with a substituted awl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted awl.

"Patient" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Prodrug" refers to a derivative of an active 4-pyrimidineamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking one or more functional groups in an active 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it can be catalyzed or induced by another agent, such as an enzyme, light, an acid or base, or a change of or exposure to a physical or environmental parameter, such as temperature. The agent can be endogenous to the conditions of use, such as an enzyme present in the cells to which the prodrug is administered or the acidic conditions of the stomach, or it can be supplied exogenously.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH3 includes the progroup C(O)CH3.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount includes an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

One of ordinary skill in the art will appreciate that compounds of the invention may exhibit the phenomena of tautomerism, conformational isomerism, geometric isomerism, and/or optical isomerism. For example, the compounds and prodrugs of the invention can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, the compounds of the invention can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the invention encompasses any tautomeric, conformational isomeric, optical isomeric, and/or geometric isomeric forms of the compounds described herein, as well as mixtures of these various different isomeric forms. In cases of limited rotation, e.g. around the 2,4-pryimidinediamine core structure, atropisomers are also possible and are also specifically included in the compounds of the invention. It is intended that the compounds encompassed herein are, with the exception of forms of isomerism, chemically stable and isolable.

As is understood by one of ordinary skill in the art, certain atoms occur in more than one isotopic form. For example hydrogen occurs as protium ($^1$H), deuterium ($^2$H) and tritium ($^3$H), and carbon occurs naturally as three different isotopes, $^{12}$C, $^{13}$C and $^{14}$C. Thus the presently disclosed formulas include compounds having one or more different isotopic forms of certain elements, including hydrogen and carbon. In one embodiment of the disclosure, the presently disclosed compounds are provided in isotopically enriched form. In particular examples, compounds of formula I are enriched in deuterium relative to protium.

Deuterium has a natural abundance of about 0.015%. Accordingly, for approximately every 6,500 hydrogen atoms occurring in nature, there is one deuterium atom. Disclosed herein are compounds enriched in deuterium at one or more positions. Thus, deuterium containing compounds of the disclosure have deuterium at one or more positions (as the case may be) in an abundance of greater than 0.015%.

In one embodiment, a compound of formula (I), at a position designated as having deuterium, has a minimum isotopic enrichment factor of at least 2000 (30% deuterium incorporation) at each atom designated as deuterium in the compound, or at least 3000 (45% deuterium incorporation).

In other embodiments, a compound of formula (I) has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Similarly, it is understood that the above definitions are not intended to include impermissible substitution patterns (e.g., methyl substituted with 5 fluoro groups). Such impermissible substitution patterns are easily recognized by a person having ordinary skill in the art.

C. Compounds of the Invention

Disclosed herein are novel 2,4-pyrimidinediamine compounds, prodrugs of the compounds, methods of making the compounds, and methods of using these compounds in the treatment of conditions in which targeting of the JAK pathway or modulation, including inhibition, of JAK kinases, particularly JAK3, are therapeutically useful. These conditions include, but are not limited to, leukemia, lymphoma, transplant rejection (e.g., pancreas islet transplant rejection, heart transplant rejection, kidney transplant rejection, liver transplant rejection, lung transplant rejection), bone marrow transplant applications (e.g., graft-versus-host disease), autoimmune diseases (e.g., diabetes), and inflammation (e.g., asthma, allergic reactions, ocular disorders). Given the severity and prevalence of these diseases and conditions, new therapies are needed.

Generally, the 2,4-pyrimidinediamine compounds of the invention are characterized by a bis-phenyl 2,4-pyrimidinediamine where one phenyl group bears at least a sulfonamide and the other phenyl group bears at least a sulfonyl urea. More specifically, a compound of formula I:

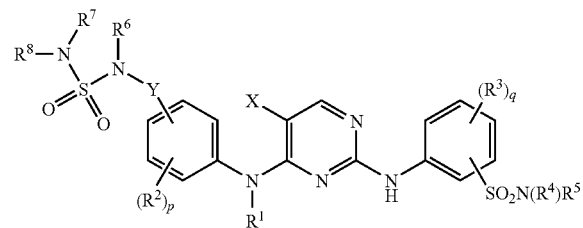

I wherein:
p is 0, 1, 2, or 3;
q is 0, 1, 2, or 3;
X is hydrogen, alkyl, substituted alkyl, hydroxy, alkoxy, substituted alkoxy, amino, substituted amino, carboxyl, carboxyl ester, —C(O)N($R^4$)$R^5$, cyano, halo, nitro, alkenyl, substituted alkenyl, alkynyl, substituted alkynyl, cycloalkynyl or substituted cycloalkynyl;
Y is a straight or branched chain $C_{1-6}$ alkylene group, cycloalkylene or substituted cycloalkylene;
$R^1$ is hydrogen, alkyl, substituted alkyl, cycloalkyl or substituted cycloalkyl;
each $R^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N($R^4$)$R^5$, nitro or halo;
each $R^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;
each $R^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or $M^+$, wherein $M^+$, a counterion, is $K^+$, $Na^+$, $Li^+$ or $^+N(R^9)_4$, wherein each $R^9$ independently is hydrogen or alkyl, and the nitrogen immediately adjacent to $R^5$ is anionic; or $R^4$ and $R^5$ together with the intervening atom or atoms bound thereto, form a heterocyclyl or substituted heterocyclyl group;
each $R^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;
$R^6$ is hydrogen, alkyl, substituted alkyl, cycloalkyl, substituted cycloalkyl, heterocyclyl, substituted heterocyclyl, aryl, substituted aryl, heteroaryl, substituted heteroaryl and acyl;
$R^6$ is a straight or branched chain $C_{1-6}$ alkylene group, cycloalkylene or substituted cycloalkylene, linking the nitrogen bearing $R^6$ and the ring bearing Y
$R^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
$R^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
optionally, $R^7$ and $R^8$, together with nitrogen to which they are bound, form a heterocyclyl or substituted heterocyclyl group;
wherein at least one of $R^7$ and $R^8$ is non-hydrogen; and
each of $R^6$, $R^7$, and $R^8$ optionally are $M^+$, wherein $M^+$ a counter-ion, is $K^+$, $Na^+$, $Li^+$ or $^+N(R^9)_4$, wherein each $R^9$ independently is hydrogen or alkyl, and the nitrogen bearing $M^+$ is anionic.

One embodiment is a compound of structural formula I where $R^1$ is hydrogen. In another embodiment, where $R^1$ is hydrogen, X is alkyl, substituted alkyl or halo.

Another embodiment is a compound of structural formula I where $R^4$ is hydrogen and $R^5$ is hydrogen.

Another embodiment is a compound of structural formula I where Y is methylene.

Another embodiment is a compound of structural formula I where $R^6$ is hydrogen, $R^7$ is $C_{1-3}$ alkyl and $R^8$ is $C_{1-3}$ alkyl.

Another embodiment is a compound of structural formula I where each of $R^2$ and $R^3$, independently, is lower alkyl or lower alkoxy.

Another embodiment is a compound of structural formula II:

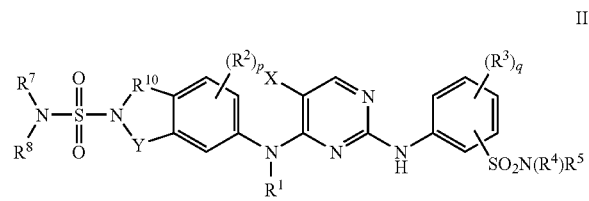

II wherein
p is 0, 1, 2, or 3;
q is 0, 1, 2, or 3;
X is hydrogen, alkyl, substituted alkyl, hydroxy, alkoxy, substituted alkoxy, amino, substituted amino, carboxyl, carboxyl ester, —C(O)N($R^4$)$R^5$, cyano, halo, nitro, alkenyl, substituted alkenyl, alkynyl, substituted alkynyl, cycloalkynyl or substituted cycloalkynyl;

Y is a straight or branched chain $C_{1-6}$ alkylene group, cycloalkylene or substituted cycloalkylene;

$R^1$ is hydrogen, alkyl, substituted alkyl, cycloalkyl or substituted cycloalkyl;

each $R^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N(R$^4$)R$^5$, nitro or halo;

each $R^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;

each $R^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or M$^+$ wherein M$^+$ is K$^+$, Na$^+$, Li$^+$ or $^+$N(R$^9$)$_4$, wherein each $R^9$ independently is hydrogen or alkyl, and the nitrogen immediately adjacent to R$^5$ is anionic; or $R^4$ and $R^5$ together with the intervening atom or atoms bound thereto, form a heterocyclyl or substituted heterocyclyl group;

each $R^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;

$R^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

$R^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or $R^7$ and $R^8$ together, with nitrogen to which they are bound, form a heterocyclyl or substituted heterocyclyl group;

$R^{10}$ is a straight or branched chain $C_{1-6}$ alkylene group, cycloalkylene or substituted cycloalkylene; and each of $R^7$ and $R^8$ optionally are M$^+$, wherein M$^+$ is K$^+$, Na$^+$, Li$^+$ or $^+$N(R$^9$)$_4$, wherein each $R^9$ independently is hydrogen or alkyl, and the nitrogen bearing M$^+$ is anionic.

Another embodiment is a compound of structural formula II, where p is zero and each of $R^6$ and Y, independently, is a straight or branched chain $C_{1-6}$ alkylene group.

Another embodiment is a compound of structural formula II where each of $R^6$ and Y, independently, is methylene or ethylene.

Another embodiment is a compound of structural formula III:

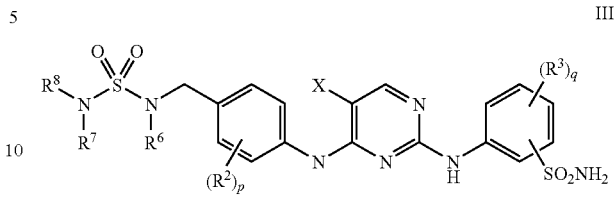

wherein:
p is 0, 1, 2, or 3;
q is 0, 1, 2, or 3;
X is alkyl, substituted alkyl, hydroxy, alkoxy, substituted alkoxy, amino, substituted amino, carboxyl, carboxyl ester, —C(O)N(R$^4$)R$^5$, cyano, halo, nitro, alkenyl, substituted alkenyl, alkynyl, substituted alkynyl, cycloalkynyl or substituted cycloalkynyl;

each $R^2$ independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy, —C(O)N(R$^4$)R$^5$ or halo;

each $R^3$ independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy or halo;

$R^6$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

$R^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

$R^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or $R^7$ and $R^8$ together, with nitrogen to which they are bound, form a heterocyclyl or substituted heterocyclyl group;

wherein at least one of $R^7$ and $R^8$ is non-hydrogen; and each of $R^6$, $R^7$, and $R^8$ optionally are substituted with M$^+$, wherein M$^+$ is K$^+$, Na$^+$, Li$^+$ or $^+$N(R$^9$)$_4$, wherein each $R^9$ independently is hydrogen or alkyl, and the nitrogen bearing M$^+$ is anionic.

Another embodiment is a compound of structural formula IV:

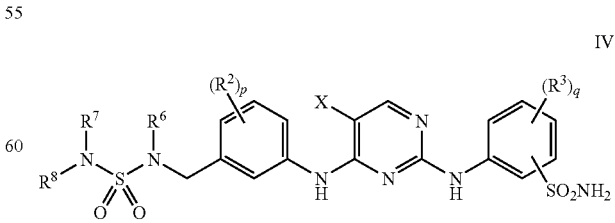

wherein:
p is 0, 1, 2, or 3;
q is 0, 1, 2, or 3;

X is alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl;

each R² independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy, —C(O)N(R⁴)R⁵ or halo;

each R³ independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy or halo;

R⁶ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

R⁷ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

R⁸ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or R⁷ and R⁸ together, with nitrogen to which they are bound, form a heterocyclyl or substituted heterocyclyl group;

wherein at least one of R⁷ and R⁸ is non-hydrogen; and each of R⁶, R⁷, and R⁸ optionally are substituted with M⁺ wherein M⁺ is K⁺, Na⁺, Li⁺ or ⁺N(R⁹)₄, wherein each R⁹ independently is hydrogen or alkyl, and the nitrogen bearing M⁺ is anionic.

Another embodiment is a compound selected from Tables I and II, or stereoisomer, tautomer, prodrug, solvate, or pharmaceutically acceptable salt thereof.

TABLE I

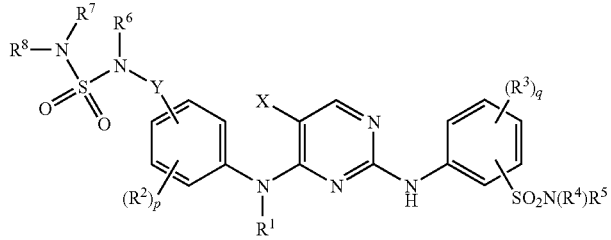

| # | —YN(R⁶)SO₂N(R⁷)R⁸ | R² | R¹ | X | R³ | —SO₂N(R⁴)R⁵ |
|---|---|---|---|---|---|---|
| I-1 | 4-CH₂NHSO₂N(CH₃)₂ | — | H | chloro | — | 3-SO₂NH₂ |
| I-2 | 4-CH₂NHSO₂N(CH₃)₂ | — | H | chloro | — | 4-SO₂NH₂ |
| I-3 | 4-CH₂NHSO₂N(CH₃)₂ | — | H | methyl | — | 3-SO₂NH₂ |
| I-4 | 4-CH₂NHSO₂N(CH₃)₂ | — | H | methyl | — | 4-SO₂NH₂ |
| I-5 | 4-CH₂NHSO₂NHCH₂CH₃ | — | H | chloro | — | 3-SO₂NH₂ |
| I-6 | 4-CH₂NHSO₂NHCH₂CH₃ | — | H | chloro | — | 4-SO₂NH₂ |
| I-7 | 4-CH₂NHSO₂NHCH₂CH₃ | — | H | methyl | — | 3-SO₂NH₂ |
| I-8 | 4-CH₂NHSO₂NHCH₂CH₃ | — | H | methyl | — | 4-SO₂NH₂ |
| I-9 | 3-CH₂NHSO₂NHCH₂CH₃ | — | H | chloro | — | 3-SO₂NH₂ |
| I-10 | 3-CH₂NHSO₂NHCH₂CH₃ | — | H | chloro | — | 4-SO₂NH₂ |
| I-11 | 3-CH₂NHSO₂NHCH₂CH₃ | — | H | methyl | — | 3-SO₂NH₂ |
| I-12 | 3-CH₂NHSO₂NHCH₂CH₃ | — | H | methyl | — | 4-SO₂NH₂ |
| I-13 | 3-CH₂NHSO₂NHCH₂CH₃ | — | H | fluoro | — | 3-SO₂NH₂ |
| I-14 | 3-CH₂NHSO₂NHCH₂CH₃ | — | H | fluoro | — | 4-SO₂NH₂ |
| I-15 | 4-CH₂NHSO₂NHCH₂CH₃ | 2-methyl | H | chloro | — | 3-SO₂NH₂ |
| I-16 | 4-CH₂NHSO₂NHCH₂CH₃ | 2-methyl | H | chloro | — | 4-SO₂NH₂ |
| I-17 | 4-CH₂NHSO₂NHCH₂CH₃ | 2-methyl | H | chloro | 3,5-dimethyl | 4-SO₂NH₂ |
| I-18 | 4-[cyclopropyl sulfamide CH₂] | — | H | chloro | — | 3-SO₂NH₂ |
| I-19 | 4-[cyclopropyl sulfamide CH₂] | — | H | chloro | — | 4-SO₂NH₂ |
| I-20 | 4-[cyclopropyl sulfamide CH₂] | — | H | chloro | 3,5-dimethyl | 4-SO₂NH₂ |

TABLE I-continued

| # | —YN(R⁶)SO₂N(R⁷)R⁸ | R² | R¹ | X | R³ | —SO₂N(R⁴)R⁵ |
|---|---|---|---|---|---|---|
| I-21 | 4- (CH₂NHSO₂NH-cyclopropyl) | — | H | methyl | — | 3-SO₂NH₂ |
| I-22 | 4- (CH₂NHSO₂NH-cyclopropyl) | — | H | methyl | — | 4-SO₂NH₂ |
| I-23 | 4- (CH₂NHSO₂NH-cyclopropyl) | — | H | methyl | 3,5-dimethyl | 4-SO₂NH₂ |
| I-24 | 4- (CH₂NHSO₂NH-cyclopropyl) | 2-methyl | H | chloro | — | 3-SO₂NH₂ |
| I-25 | 4- (CH₂NHSO₂NH-cyclopropyl) | 2-methyl | H | chloro | — | 4-SO₂NH₂ |
| I-26 | 4- (CH₂NHSO₂NH-cyclopropyl) | 2-methyl | H | chloro | 3,5-dimethyl | 4-SO₂NH₂ |
| I-27 | 3- (diacyl sulfamide with ethyl) | — | H | methyl | — | 3-SO₂NHC(O)CH₂CH₃ |
| I-28 | 3- (diacyl sulfamide with ethyl) | — | H | methyl | — | 3-SO₂NHC(O)CH₂CH₃ |
| I-29 | 3-CH₂NHSO₂NHCH₂CH₃ | — | H | methyl | 4-methyl | 3-SO₂NH₂ |
| I-30 | 3-CH₂NHSO₂N(CH₃)₂ | — | H | methyl | — | 3-SO₂NH₂ |
| I-31 | 3-CH₂NHSO₂N(CH₃)₂ | — | H | methyl | — | 4-SO₂NH₂ |
| I-32 | 3-CH₂NHSO₂N(CH₃)₂ | — | H | methyl | 4-methyl | 3-SO₂NH₂ |

TABLE II

II

[Structure: R⁷R⁸N-S(O)₂-N(R⁶)-Y-[benzene ring with p(R²)]-X-[pyrimidine with N]-NH-[benzene ring with (R³)q and SO₂N(R⁴)R⁵], with R¹ on the N linker]

| # | R⁷ | R⁸ | Y | R⁶ | R² | R¹ | X | R³ | —SO₂N(R⁴)R⁵ |
|---|----|----|---|----|----|----|----|----|-------------|
| II-1 | Me | Me | —CH₂— | —(CH₂)₂— | — | H | F | 4-Me | 3-SO₂NH₂ |
| II-2 | Me | Me | —CH₂— | —CH₂— | — | H | F | 4-Me | 3-SO₂NH₂ |
| II-3 | Me | Me | —CH₂— | —CH₂— | — | H | Me | — | 4-SO₂NH₂ |
| II-4 | Me | Me | —CH₂— | —CH₂— | — | H | Me | — | 3-SO₂NH₂ |
| II-5 | Me | Me | —CH₂— | —CH₂— | — | H | Me | 4-Me | 3-SO₂NH₂ |

Prodrugs

Those of skill in the art will appreciate that the 2,4-pyrimidinediamine compounds described herein can include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical and can be caused, for example, by hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups can be designed to metabolize in the presence of enzymes such as esterases, amidases, lipolases, and phosphatases, including ATPases and kinase, etc. Progroups including linkages capable of metabolizing in vivo are well known and include, by way of example and not limitation, ethers, thioethers, silylethers, silylthioethers, esters, thioesters, carbonates, thiocarbonates, carbamates, thiocarbamates, ureas, thioureas, and carboxamides. In some instances, a "precursor" group that is oxidized by oxidative enzymes such as, for example, cytochrome $P_{450}$ of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), and carboxyls. A wide variety of progroups, as well as the resultant promoieties, suitable for masking functional groups in active 2,4-pyrimidinediamine compounds to yield prodrugs are well-known in the art. For example, a hydroxyl functional group can be masked as a sulfonate, ester, or carbonate promoiety, which can be hydrolyzed in vivo to provide the hydroxyl group. An amino functional group can be masked as an amide, carbamate, imine, urea, phosphenyl, phosphoryl, or sulfenyl promoiety, which can be hydrolyzed in vivo to provide the amino group. A carboxyl group can be masked as an ester (including silyl esters and thioesters), amide, or hydrazide promoiety, which can be hydrolyzed in vivo to provide the carboxyl group. Other specific examples of suitable progroups and their respective promoieties will be apparent to those of skill in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4-pyrimidinediamine, the N4 nitrogen atom of the 2,4-pyrimidinediamine, and/or a primary or secondary nitrogen atom included in a substituent on the 2,4-pyrimidinediamine.

As noted above, the identity of the progroup is not critical, provided that it can be metabolized under the desired conditions of use, for example, under the acidic conditions found in the stomach and/or by enzymes found in vivo, to yield a biologically active group, e.g., the 2,4-pyrimidinediamines as described herein. Thus, skilled artisans will appreciate that the progroup can include virtually any known or later-discovered hydroxyl, amine or thiol protecting group. Non-limiting examples of suitable protecting groups can be found, for example, in Protective Groups in Organic Synthesis, Greene & Wuts, 2$^{nd}$ Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, and targeting-specific transporters. Groups capable of imparting prodrugs with these characteristics are well-known and are described, for example, in Ettmayer et al., 2004, *J. Med. Chem.* 47(10):2393-2404, the disclosure of which is incorporated by reference. All of the various groups described in these references can be utilized in the prodrugs described herein.

A particularly useful progroup of the invention is —CH$_2$OP(OH)$_2$ as well as esters, mixed acid esters and salts thereof. In some embodiments, the —CH$_2$OP(OH)$_2$ progroup is attached via an NH, annular or not, of the parent molecule. There can be more than one such progroup. Thus, one embodiment is a compound of formula V,

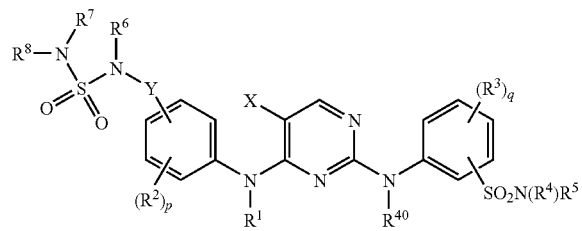

V or solvate thereof, where R$^2$, R$^3$, R$^4$, R$^5$, R$^6$, R$^7$, R$^8$, X, p and q are as defined in the summary and detailed description, R$^{40}$ is H or R$^{50}$, and at least one of R$^4$, R$^5$, R$^6$, R$^7$, R$^8$ and R$^{40}$ is R$^{50}$; where R$^{50}$ is —CH$_2$OP(O)(OR$^{11}$)$_2$; each is independently H, C$_{1-6}$alkyl or a monovalent cationic group, or two together with the atoms to which they are attached, form a 4-8 membered cyclic phosphate group

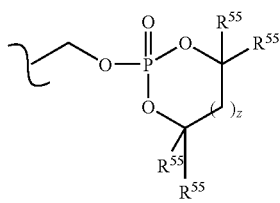

where each R$^{55}$ is independently H, optionally substituted C$_{1-6}$alkyl, optionally substituted 3-8 membered heteroalicyclyl, optionally substituted C$_{6-14}$aryl, optionally substituted C$_{7-20}$arylalkyl, optionally substituted 5-14 membered heteroaryl or optionally substituted 6-15 membered heteroarylalkyl; z is 0, 1, 2 or 3; or two R$^{11}$ together represent a divalent cationic group selected from Ba$^{2+}$, Bi$^{2+}$, Ca$^{2+}$, Cu$^{2+}$, Mg$^{2+}$, Ni$^{2+}$, Sr$^{2+}$ and Zn$^{2+}$.

In one embodiment, the cyclic phosphate group is a 5 or 6-membered cyclic phosphate group, where —CH$_2$OP(O)(OR$^{11}$)$_2$ is

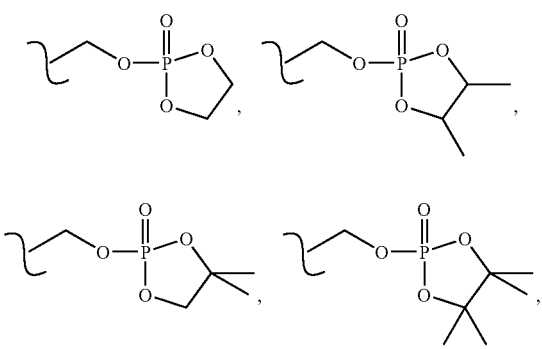

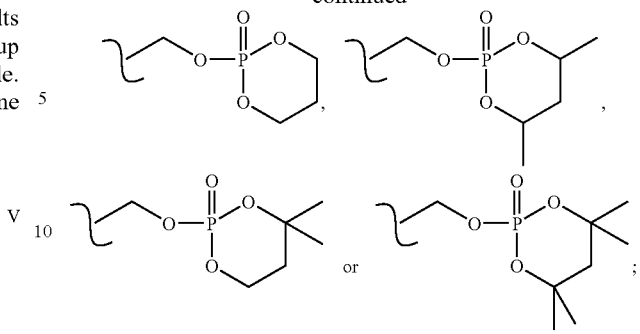

or two R$^{11}$ together represent a divalent cationic group selected from Ca$^{2+}$, Mg$^{2+}$ and Zn$^{2+}$.

Another embodiment is a compound of formula VI,

VI

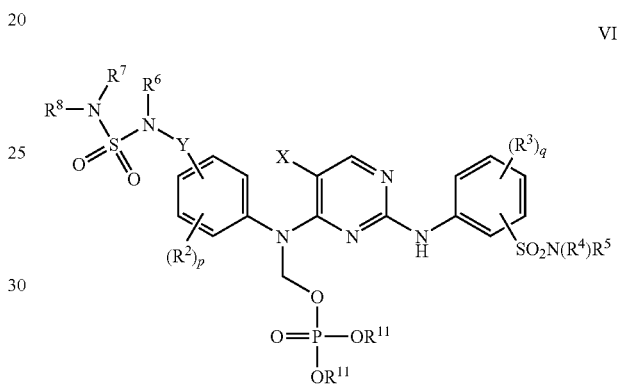

or solvate thereof, where R$^2$, R$^3$, R$^4$, R$^5$, R$^6$, R$^7$, R$^8$, X, p and q are as defined in the summary and detailed description, and R$^{11}$ is defined as above.

While not intending to be bound by any particular theory of operation, it is believed that progroups —CH$_2$OP(O)(OR$^{11}$)$_2$, e.g according to formula VI, metabolize to active compounds of the invention via the corresponding hydroxymethylamine intermediate illustrated below:

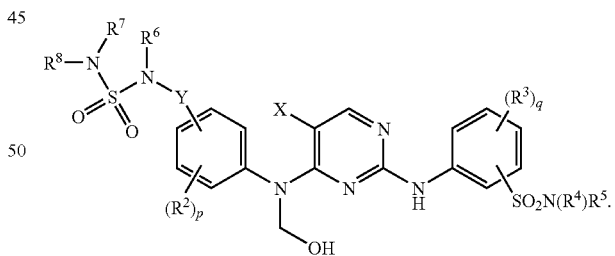

Such hydroxymethylamine compounds, although isolable, are known to be unstable under physiological conditions and various pH ranges where they hydrolyze in vivo to yield formaldehyde and the active drug substance. Based on this observation, compounds of the invention include hydroxymethyl progroups that can be metabolized in vivo, for example by the acidic conditions of the stomach and/or by enzymes present in the digestive tract or other organs and/or tissues or fluids with the body, to yield the active drug substance 2,4-pyrimidinediamine.

Moreover, it is expected that the amino and thio analogs of these hydroxymethylamines, will be similarly unstable at physiological conditions and also hydrolyze in vivo to the active 2,4-pyrimdiendiamine drug. Accordingly, compounds of the invention include these corresponding primary amino and thiol compounds. Also, the invention includes compounds in which the primary amine, thiol and hydroxy groups are masked with "protecting" groups that are removed under physiological conditions of use to yield the corresponding hydroxymethyl, thiol methyl and aminomethyl compounds, that is, with these "protecting groups" these compounds will likewise make suitable prodrugs.

Suitability of any particular progroup for a desired mode of administration can be confirmed in biochemical assays. For example, if a prodrug is to be administered by injection into a particular tissue or organ and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-pyrimidinediamine compound with tissue and/or organ extracts. Using tissue and/or organ extracts can be of particular convenience when the identity(ies) of the enzymes expressed in the target tissues or organs are unknown or in instances when the isolated enzymes are not conveniently available. Skilled artisans will be able to readily select progroups having metabolic properties (such as kinetics) suitable for particular applications using such in vitro tests. Specific prodrugs could also be tested for suitable metabolism in vitro animal models.

Compounds of the invention bearing the —CH$_2$OP(O)(OR$^{11}$)$_2$ progroup can be synthesized, e.g., as depicted below for compounds of formula VI, for example, when appropriate protecting groups are installed elsewhere in the molecule.

The 2,4-pyrimidinediamine compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed.

One embodiment is a pharmaceutical formulation including a compound of formula I, as described herein, or a prodrug thereof, and at least one pharmaceutically acceptable excipient, diluent, preservative, stabilizer, or mixture thereof.

The compounds can be provided in a variety of formulations and dosages. The compounds can be provided in a pharmaceutically acceptable form, including where the compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed. It is to be understood that reference to the compound, 2,4-pyrimidinediamine compound, or "active" in discussions of formulations is also intended to include, where appropriate as known to those of skill in the art, formulation of the prodrugs of the 2,4-pyrimidinediamine compounds. In one embodiment, the compounds are provided as non-toxic pharmaceutically acceptable salts, as noted previously. Suitable pharmaceutically acceptable salts of the compounds described herein include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine

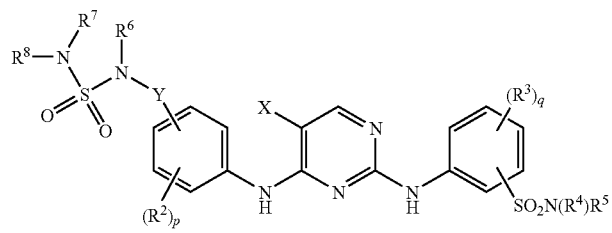
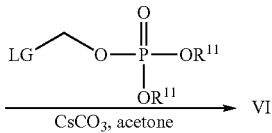

Typically, the proton on the 4-NH of the pyrimidinediamine system can be selectively alkylated over the 2-NH with the appropriate phosphonate reagent and reaction conditions, where LG is a suitable leaving group to form compounds of the invention, in this case of formula VI. Further description of how to make progroups of formula —CH$_2$OP(O)(OR$^{11}$)$_2$ as described herein is specifically taught in U.S. Pat. No. 7,449,458, entitled "Pyrimidinediamine Prodrugs and their Uses," the disclosure of which is hereby incorporated by reference in its entirety.

Pharmaceutical Compositions

Another embodiment is a pharmaceutical composition including a compound as described in any of the embodiments above. Pharmaceutical compositions described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

groups can also include quaternary ammonium salts in which the amino nitrogen atom carries a suitable organic group such as an alkyl, alkenyl, alkynyl, or substituted alkyl moiety. Furthermore, where the compounds of the invention carry an acidic moiety, suitable pharmaceutically acceptable salts thereof can include metal salts such as alkali metal salts, e.g., sodium or potassium salts; and alkaline earth metal salts, e.g., calcium or magnesium salts.

The pharmaceutical compositions for the administration of the 2,4-pyrimidinediamine compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect.

The 2,4-pyrimidinediamine compounds can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. In addition to the treatment of warm-blooded animals such as mice, rats, horses, cattle, sheep, dogs, cats, and monkeys, the compounds described herein can be effective in humans.

Administration of the compounds described herein, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

D. Methods of the Invention

The present invention provides 2,4-pyrimidinediamine compounds and prodrugs thereof, as described herein, for use in therapy for the conditions described herein. The present invention further provides use of the compounds of the present invention in the manufacture of a medicament for the treatment of conditions in which targeting of the JAK pathway or inhibition of JAK kinases, particularly JAK3, are therapeutically useful. The methods include conditions where the function of lymphocytes, macrophages, or mast cells is involved. Conditions in which targeting of the JAK pathway or inhibition of the JAK kinases, particularly JAK3, are therapeutically useful include leukemia, lymphoma, transplant rejection (e.g., pancreas islet transplant rejection), bone marrow transplant applications (e.g., graft-versus-host disease)), autoimmune diseases (e.g., rheumatoid arthritis, etc.), inflammation (e.g., asthma, etc.) and other conditions as described in greater detail herein.

As noted previously, numerous conditions can be treated using the 2,4-substituted pyrimidinediamine compounds, prodrugs thereof, and methods of treatment as described herein. As used herein, "Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

The compounds described herein are potent and selective inhibitors of JAK kinases and are particularly selective for cytokine signaling pathways containing JAK3. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds may also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "*JAK kinase mediated diseases*"). Non-limiting examples of JAK kinase mediated diseases that can be treated or prevented with the compounds include, but are not limited to, the following: allergies; asthma; autoimmune diseases such as transplant rejection (e.g., kidney, heart, lung, liver, pancreas, skin; host versus graft reaction (HVGR), and graft versus host reaction (GVHR)), rheumatoid arthritis, and amyotrophic lateral sclerosis; T-cell mediated autoimmune diseases such as multiple sclerosis, psoraiasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliteraus and primary pulmonary hypertension; solid, delayed Type IV hypersensitivity reactions; and hematologic malignancies such as leukemia and lymphomas.

One embodiment is a method of inhibiting an activity of a JAK kinase, including contacting the JAK kinase with an amount of a compound, effective to inhibit an activity of the JAK kinase, of formula I:

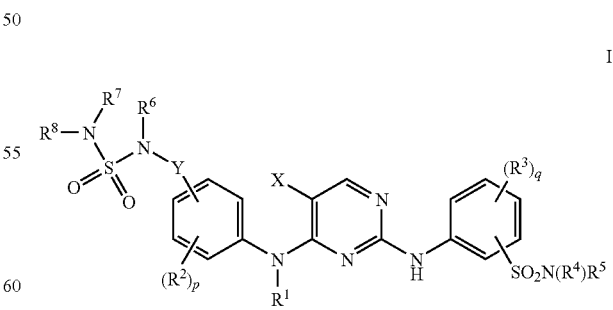

wherein:
p is 0, 1, 2, or 3;
q is 0, 1, 2, or 3;
X is hydrogen, alkyl, substituted alkyl, hydroxy, alkoxy, substituted alkoxy, amino, substituted amino, carboxyl, carboxyl ester, —C(O)N(R$^4$)R$^5$, cyano, halo, nitro, alkenyl, substituted alkenyl, alkynyl, substituted alkynyl, cycloalkynyl or substituted cycloalkynyl;

Y is a straight or branched chain C$_{1-6}$ alkylene group, cycloalkylene or substituted cycloalkylene;

R$^1$ is hydrogen, alkyl, substituted alkyl, cycloalkyl or substituted cycloalkyl;

each R$^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N(R$^4$)R$^5$, nitro or halo;

each R$^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;

each R$^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or M$^+$ wherein M$^+$ is K$^+$, Na$^+$, Li$^+$ or $^+$N(R$^9$)$_4$, wherein each R$^9$ independently is hydrogen or alkyl, and the nitrogen immediately adjacent to R$^5$ is anionic; or R$^4$ and R$^5$ together with the intervening atom or atoms bound thereto, form a heterocyclyl or substituted heterocyclyl group;

each R$^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;

R$^6$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or R$^6$ is a straight or branched chain C$_{1-6}$alkylene group, cycloalkylene or substituted cycloalkylene, linking the nitrogen bearing R$^6$ and the ring bearing Y R$^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

R$^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or R$^7$ and R$^8$ together, with nitrogen to which they are bound, form a heterocyclyl or substituted heterocyclyl group;

wherein at least one of R$^7$ and R$^8$ is non-hydrogen; and
each of R$^6$, R$^7$, and R$^8$ optionally are M$^+$, wherein M$^+$ is K$^+$, Na$^+$, Li$^+$ or $^+$N(R$^9$)$_4$, wherein each R$^9$ independently is hydrogen or alkyl, and the nitrogen bearing M$^+$ is anionic.

In the various method embodiments below, when the compound of Formula I is referred to, also meant to be included are distinct and analogous embodiments that apply to compounds of formula II, III and W, as well as to species I-1 through I-32 and II-1 through II-5.

In another embodiment, this invention provides a method of inhibiting an activity of a JAK kinase, including contacting the JAK kinase with an amount of a compound effective to inhibit an activity of the JAK kinase, where the compound is according to formula I, as described herein. In certain embodiments of the methods described herein, the method is carried out in vivo.

In another embodiment, this invention provides a method of inhibiting an activity of a JAK kinase, including contacting in vitro a JAK3 kinase with an amount of a compound effective to inhibit an activity of the JAK kinase, where the compound is according to formula I, as described herein.

In a specific embodiment, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompability) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophapges and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type W hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the 2,4-pyrimidinediamine compounds described herein can be used to treat and/or prevent many aspects of transplant rejection, and are particularly useful in the treatment and/or prevention of rejection reactions that are mediated, at least in part, by T-cells, such as HVGR or GVHR. The 2,4-pyrimidinediamine compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, including administering to a patient suffering from such an autoimmune disease an amount of a compound effective to treat the autoimmune disease where the compound is according to formula I, as described herein. In certain embodiments of the methods the autoimmune disease is multiple sclerosis (MS), psoriasis, or Sjogran's syndrome.

Therapy using the 2,4-pyrimidinediamine compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand name SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the 2,4-pyrimidinediamine compounds could be administered either in combination or adjunctively with an inhibitor of a Syk kinase. Syk kinase is a tyrosine kinase known to play a critical role in Fcγ receptor signaling, as well as in other signaling cascades, such as those involving B-Cell receptor signaling (Turner et al., (2000), Immunology Today 21:148-154) and integrins beta(1), beta (2), and beta (3) in neutrophils (Mocsavi et al., (2002), Immunity 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003 (publication no. 2007/0060603); WO 2004/014382; Ser. No. 10/903,263 filed Jul. 30, 2004 (publication no. 2005/0234049); PCT/US2004/24716 filed Jul. 30, 2004 (WO005/016893); Ser. No. 10/903,870 filed Jul. 30, 2004 (publication no. 2005/0209224); PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The 2,4-pyrimidinediamine described herein and Syk inhibitory compounds could be used alone or in combination with one or more conventional transplant rejection treatments, as described above.

In a specific embodiment, the 2,4-pyrimidinediamine compounds can be used to treat or prevent these diseases in patients that are either initially non-responsive (resistant) to or that become non-responsive to treatment with a Syk inhibitory compound or one of the other current treatments for the particular disease. The 2,4-pyrimidinediamine compounds could also be used in combination with Syk inhibitory compounds in patients that are Syk-compound resistant or non-responsive. Suitable Syk-inhibitory compounds with which the 2,4-pyrimidinediamine compounds can be administered are provided supra.

In another embodiment, this invention provides a method of treating a T-cell mediated autoimmune disease, including administering to a patient suffering from such an autoimmune disease an amount of a compound according to formula I, in combination with or adjunctively to a compound that inhibits Syk kinase with an $IC_{50}$ of at least 10 μM, effective to treat the autoimmune disease.

In another embodiment, this invention provides a method of treating or preventing allograft transplant rejection, either acute or chronic, in a transplant recipient, including administering to the transplant recipient an amount of a compound according to formula I effective to treat or prevent the rejection. In a further embodiment, the compound is administered to a tissue or an organ prior to or concurrent with, transplanting the tissue or organ in the transplant recipient. In another embodiment, the compound is administered to the tissue or organ and the patient. In a specific embodiment the allograft transplant rejection is mediated by HVGR or GVHR. In another embodiment, the allograft transplant organ is a kidney, a heart, a liver, or a lung. In another embodiment, in which the allograft transplant organ is a kidney, a heart, a liver, or a lung, the compound is administered in combination with or adjunctively to another immunosuppressant. In a more specific embodiment, the immunosuppressant is cyclosporine, tacrolimus, sirolimus, an inhibitor of IMPDH, mycophenolate, mycophanolate mofetil, an anti-T-Cell antibody or OKT3.

The 2,4-pyrimidinediamine compounds described herein are cytokine moderators of IL-4 signaling. As a consequence, the 2,4-pyrimidinediamine compounds could slow the response of Type I hypersensitivity reactions. Thus, in a specific embodiment, the 2,4-pyrimidinediamine compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the 2,4-pyrimidinediamine compounds can be administered singly, as mixtures of one or more 2,4-pyrimidinediamine compounds, or in mixture or combination with other agents useful for treating such diseases and/or the symptoms associated with such diseases. The 2,4-pyrimidinediamine compounds can also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, rituximab, PD4 inhibitors, p38 inhibitors, PDE4 inhibitors, and antihistamines, to name a few. The 2,4-pyrimidinediamine compounds can be administered per se in the form of prodrugs or as pharmaceutical compositions, including an active compound.

In another embodiment, this invention provides a method of treating or preventing a Type IV hypersensitivity reaction, including administering to a subject an amount of a compound effective to treat or prevent the hypersensitivity reaction, where the compound is according to formula I, as described herein. In one embodiment, the method is practiced prophylactically. In some embodiments, the compound is administered prior to exposure to an allergen.

In another embodiment, this invention provides a method of inhibiting a signal transduction cascade in which JAK3 kinase plays a role, including contacting a cell expressing a receptor involved in such a signaling cascade with a compound, where the compound is according to formula I, as described herein.

In another embodiment, this invention provides a method of treating or preventing a JAK kinase-mediated disease, including administering to a subject an amount of compound effective to treat or prevent the JAK kinase-mediated disease, where the compound is according to formula I, as described herein.

In another embodiment, this invention provides a method of treating or preventing a JAK kinase-mediated disease, in which the JAK-mediated disease is HVGR or GVHR, including administering to a subject an amount of compound effective to treat or prevent the JAK kinase-mediated disease, where the compound is according to formula I, as described herein.

In another embodiment, ocular disorders are treated using an effective amount of compound of formula I, as described herein. In one aspect of the disclosed method for treating ocular disorders, administration of one or more of the presently disclosed 2,4-pyrimidinediamine compounds is effective to increase tear production volume as compared to untreated tear production volume, thereby ameliorating a symptom of dry eye syndrome. In one aspect, tear production volume is increased within five days, such as in less than four days, and in some examples in less than two days. In one embodiment, tear production volume is increased by at least about 25% over initial tear production within two days of initial treatment with a presently disclosed 2,4-pyrimidinediamine compound. In other embodiments, tear production is increased at least about 30%, such as at least about 50% over initial tear production within less than two days. Increases in tear production upon administration of the present compounds results, in some instances, in tear production volume comparable to normal tear production. Typically the disclosed compounds, when used for treating ocular disorders topically, are administered at least once daily and typically at most twice a day.

As mentioned, another embodiment provides a method of treating a disease and/or disorder of the eye, which includes administering to a subject an amount of a compound effective to treat the disease and/or disorder of the eye wherein the compound is according to formula I, as described herein. Diseases and disorders of the eye include, but are not limited to, dry eye syndrome, uveitis, allergic conjunctivitus, glaucoma and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g uveitis, can cause this rise in intraocular pressure. Rosacea is a chronic inflammatory condition characterized by facial erythema but it can affect the eyes. As mentioned, compounds described herein may be used to treat inflammatory responses. While not wishing to be bound by theory, it is believed that compounds described herein are effective treatments of these eye disorders due, at least in part, to their JAK inhibitory activity.

Active compounds described herein typically inhibit the JAK/Stat pathway. The activity of a specified compound as an inhibitor of a JAK kinase can be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 μM or less.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches including the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, e.g., International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (e.g., deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

Generally cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma. More specifically, related to particular tissues, organs or areas of the body, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. The term "cancerous cell" as provided herein, includes a cell afflicted by any one of the above-identified conditions.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blake et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34; 22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group includes a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34; q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the JAK inhibitory compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8; 21)(q22; q22), AML1(CBF-alpha)/ETO, Acute promyelocytic leukemia (AML with t(15; 17)(q22; q11-12) and variants, PML/RAR-alpha), AML with abnormal bone marrow eosinophils (inv(16)(p13q22) or t(16; 16)(p13; q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

One means of assaying for such inhibition is detection of the effect of the 2,4-pyrimidinediamine compounds on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (e.g., the 2,4-substituted pyrimindinediamine compounds described herein) on the JAK1 and JAK3 kinases, human Ramos B cells are stimulated with human IL-4. 20 to 24 hours post stimulation, cells are stained for upregulation of CD23 and analyzed using flow cytometry (FACS). A reduction of the amount of CD23 present compared to control conditions indicates the test compound actively inhibits the JAK kinase pathway.

The activity of the compounds described herein can further be characterized by assaying the effect of the 2,4-pyrimidinediamine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the 2,4-pyrimidinediamine compounds in the presence of IL-2 for 72 hours, and at the assay endpoint intracellular ATP concentrations are measured to assess cell viability. A reduction in cell proliferation compared to control conditions is indicative of inhibition of the JAK kinase pathway.

The activity of the compounds described herein can additionally be characterized by assaying the effect of the 2,4-pyrimidinediamine compounds described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated.

Active compounds as described herein generally inhibit the JAK kinase pathway with an $IC_{50}$ in the range of about 1 mM or less, as measured in the assays described herein. Of course, skilled artisans will appreciate that compounds which exhibit lower $IC_{50}$s, (on the order, for example, of 100 µM, 75 µM, 50 µM, 40 µM, 30 µM, 20 µM, 15 µM, 10 µM, 5 µM, 1 µM, 500 nM, 100 nM, 10 nM, 1 nM, or even lower) can be particularly useful in therapeutic applications. In instances where activity specific to a particular cell type is desired, the compound can be assayed for activity with the desired cell type and counterscreened for a lack of activity against other cell types. The desired degree of "inactivity" in such counter screens, or the desired ratio of activity vs. inactivity, may vary for different situations and can be selected by the user.

The 2,4-pyrimidinediamine active compounds also typically inhibit IL-4 stimulated expression of CD23 in B-cells with an $IC_{50}$ in the range of about 20 µM or less, typically in the range of about 10 µM, 1 µM, 500 nM, 100 nM, 10 nM, 1 nM, or even lower. A suitable assay that can be used is the assay described in Example 2, "Assay for Ramos B-Cell Line Stimulated with IL-4." In certain embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described in Example 2.

Additionally, the 2,4-pyrimidinediamine active compounds typically inhibit an activity of human primary T-cells with an $IC_{50}$ in the range of about 20 µM or less, typically in the range of about 10 µM, 1 µM, 500 nM, 100 nM, 10 nM, 1 nM, or even lower. The $IC_{50}$ against human primary T-cells can be determined in a standard in vitro assay with isolated human primary T-cells. A suitable assay that can be used is the assay described above, "Primary Human T-cell Proliferation Assay Stimulated with IL-2." In some embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described above.

The 2,4-pyrimidinediamine active compounds also typically inhibit expression of ICAM1 (CD54) induced by IFNγ, exposure in U937 or A549 cells with an $IC_{50}$ in the range of about 20 µM or less, typically in the range of about 10 µM, 1

μM, 500 nM, 100 nM, 10 nM, 1 nM, or even lower. The $IC_{50}$ against expression of ICAM (CD54) in IFNγ stimulated cells can be determined in a functional cellular assay with an isolated A549 or U937 cell line. The active 2,4-pyrimidinediamine compounds typically have an $IC_{50}$ of less than or equal to 20 μM, greater than 20 μM, or greater than 20 μM but less than 50 μM in the assay.

E. Pharmaceutical Compositions of the Invention

Pharmaceutical compositions including the 2,4-pyrimidinediamine compounds described herein (or prodrugs thereof) can be manufactured by means of conventional mixing, dissolving, granulating, dragee-making, levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

The 2,4-pyrimidinediamine compound or prodrug can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one embodiment, this invention provides a pharmaceutical formulation including a compound selected from the compounds of this invention, as described above.

The compounds can be provided in a variety of formulations and dosages. The compounds can be provided in a pharmaceutically acceptable form including, where the compound or prodrug can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed. It is to be understood that reference to the compound, 2,4-pyrimidinediamine compound, or "active" in discussions of formulations is also intended to include, where appropriate as known to those of skill in the art, formulation of the prodrugs of the 2,4-pyrimidinediamine compounds.

In one embodiment, the compounds are provided as nontoxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also include quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention can be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the 2,4-pyrimidinediamine compounds and salts thereof, for example, hydrates.

The 2,4-pyrimidinediamine compounds may have one or more asymmetric centers, and may accordingly exist both as enantiomers and as diastereomers. It is to be understood that all such isomers and mixtures thereof are encompassed within the scope of the present invention.

The 2,4-pyrimidinediamine compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds of the invention can be effective in humans.

The pharmaceutical compositions for the administration of the 2,4-pyrimidinediamine compounds may conveniently be presented in dosage unit form and can be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

The 2,4-pyrimidinediamine compound(s) or prodrug(s) described herein, or compositions thereof, will generally be used in an amount effective to achieve the intended result, for example in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art.

As known by those of skill in the art, the preferred dosage of 2,4-pyrimidinediamine compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

In the context of transplant rejection, the compound can be administered while the patient is not having an acute rejection reaction to avoid the onset of rejection and/or prior to the appearance of clinical indications of chronic rejection. The compound can be administered systemically to the patient as well as administered to the tissue or organ prior to transplanting the tissue or organ in the patient.

Also provided are kits for administration of the 2,4-substituted pyrimidinediamine, prodrug thereof or pharmaceutical formulations including the compound, that may include a dosage amount of at least one 2,4-pyrimidinediamine or a composition including at least one 2,4-pyrimidinediamine as disclosed herein. Kits may further include suitable packaging and/or instructions for use of the compound. Kits may also include a means for the delivery of the at least one 2,4-pyrimidinediamine or compositions including at least one 2,4-substituted pyrimidinediamine, such as an inhaler, spray dispenser (e.g. nasal spray), syringe for injection or pressure pack for capsules, tables, suppositories, or other device as described herein.

It will be appreciated by one of skill in the art that the embodiments summarized above may be used together in any suitable combination to generate additional embodiments not expressly recited above, and that such embodiments are considered to be part of the present invention.

F. General Synthesis of the Compounds of the Invention

The 2,4-pyrimidinediamine compounds and prodrugs of the invention can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates thereof, are described in copending U.S. application Ser. No. 10/355,543, filed Jan. 31, 2003 (US2004/0029902A1), the contents of which are incorporated herein by reference. Suitable exemplary methods that can be routinely used and/or adapted to synthesize active 2,4-pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893), the disclosures of which are incorporated herein by reference. All of the compounds described herein (including prodrugs) can be prepared by routine adaptation of these methods.

Specific exemplary synthetic methods for the 2,4-pyrimidinediamines described herein are also described in Example 1 below. Those of skill in the art will also be able to readily adapt these examples for the synthesis of additional 2,4-pyrimidinediamines as described herein.

A variety of exemplary synthetic routes that can be used to synthesize the 2,4-pyrimidinediamine compounds of the invention are described in Schemes (I)-(VII), below. These methods can be routinely adapted to synthesize the 2,4-pyrimidinediamine compounds and prodrugs described herein.

In one exemplary embodiment, the compounds can be synthesized from substituted or unsubstituted uracils as illustrated in Scheme (I), below:

ine is obtained. The regioselectivity of the reaction can also be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions can be used: heat to 175° C. in ethanol for 5-20 min in a Smith Reactor (Personal Chemistry, Uppsala, Sweden) in a sealed tube (at 20 bar pressure).

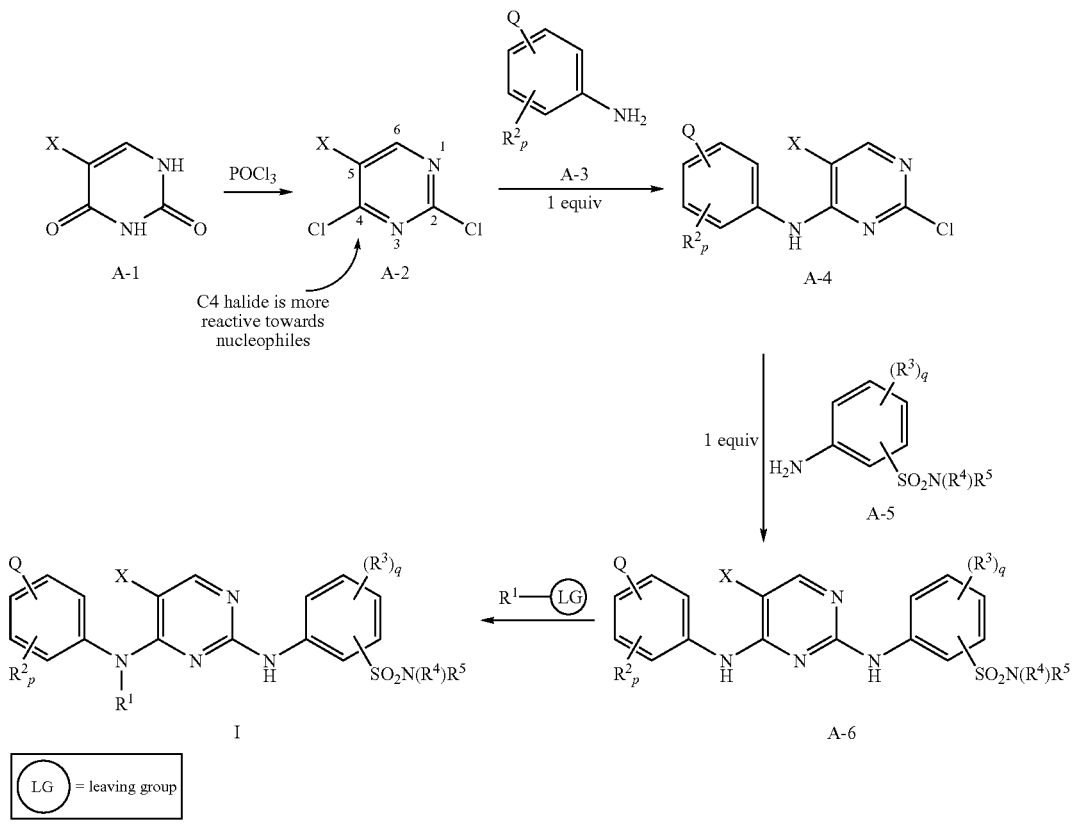

In Scheme (I), $R^1$, $(R^2)_p$, $(R^3)_q$, $R^4$, $R^5$, and X, are as defined herein, and Q is $-YN(R^6)S(O)_2N(R^7)R^8$, wherein $R^6$, $R^7$ and $R^8$ are as defined herein. According to Scheme (I), uracil A-1 is dihalogenated at the 2- and 4-positions using a standard halogenating agent such as POCl$_3$ (or other standard halogenating agent) under standard conditions to yield 2,4-dichloropyrimidine A-2. Depending upon the X substituent, in pyrimidinediamine A-2, the chloride at the C4 position is more reactive towards nucleophiles than the chloride at the C2 position. This differential reactivity can be exploited to synthesize 2,4-pyrimidinediamines I by reacting 2,4-dichloropyrimidine A-2 first with one equivalent of amine A-3, yielding 4N-substituted-2-chloro-4-pyrimidineamine A-4, and then with amine A-5, yielding a 2,4-pyrimidinediamine derivative A-6, where N4 nitrogen can be selectively alkylated to give compounds of formula I.

Typically, the C4 halide is more reactive towards nucleophiles, as illustrated in Scheme (I). However, as will be recognized by skilled artisans, the identity of the X substituent may alter this reactivity. For example, when X is trifluoromethyl, a 50:50 mixture of 4N-substituted-4-pyrimidineamine A-4 and the corresponding 2N-substituted-2-pyrimidineam- The uracil A-1 starting materials can be purchased from commercial sources or prepared using standard techniques of organic chemistry. Commercially available uracils that can be used as starting materials in Scheme (I) include, by way of example and not limitation, uracil (Aldrich #13, 078-8; CAS Registry 66-22-8); 5-bromouracil (Aldrich #85, 247-3; CAS Registry 51-20-7; 5-fluorouracil (Aldrich #85, 847-1; CAS Registry 51-21-8); 5-iodouracil (Aldrich #85, 785-8; CAS Registry 696-07-1); 5-nitrouracil (Aldrich #85, 276-7; CAS Registry 611-08-5); and 5-(trifluoromethyl)-uracil (Aldrich #22, 327-1; CAS Registry 54-20-6). Additional 5-substituted uracils are available from General Intermediates of Canada, Inc., Edmonton, Calif., and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized using standard techniques. For example, suitable amines can be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines A-3 and A-5 and/or substituent X on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis,* 3d Edition, John Wiley & Sons, Inc., New York (1999) and the references cited therein (hereinafter "Greene & Wuts").

Thus, "protecting group" refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and, additionally, in Harrison et al., *Compendium of Synthetic Organic Methods,* Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC"), and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups), aryl silyl ethers (e.g., triphenylsilyl ether), mixed alkyl and aryl substituted silyl ethers, and allyl ethers.

A specific embodiment of Scheme (I) utilizing 5-fluorouracil (Aldrich #32, 937-1) as a starting material is illustrated in Scheme (Ia), below:

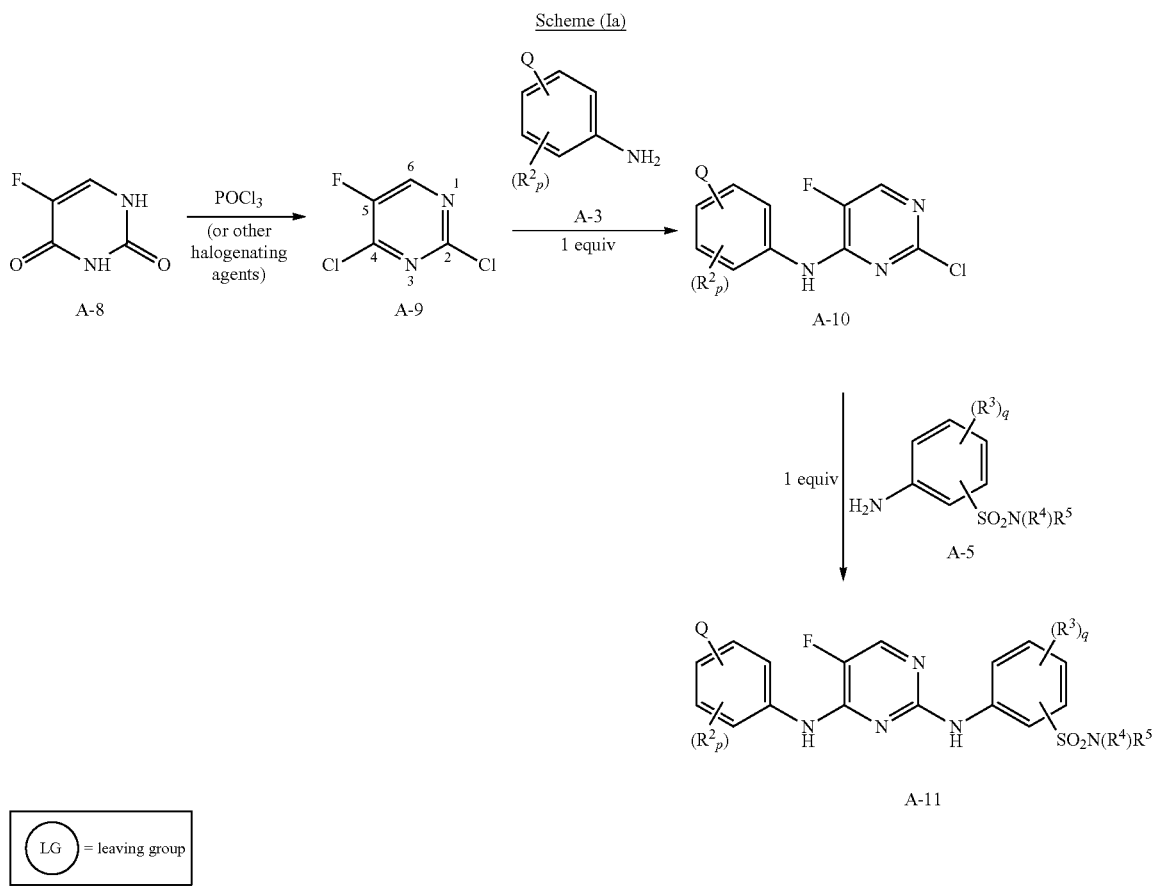

In Scheme (Ia), $(R^2)_p$, $(R^3)_q$, $R^4$, $R^5$, and Q are as previously defined for Scheme (I). Asymmetric 2N,4N-disubstituted-5-fluoro-2,4-pyrimidinediamine A-11 can be obtained by reacting 2,4-dichloro-5-fluoropyrimidine A-9 with one equivalent of amine A-3 (to yield 2-chloro-N4-substituted-5-fluoro-4-pyrimidineamine A-10) followed by one or more equivalents of amine A-5.

Myriad references teaching methods useful for synthesizing pyrimidines generally, as well as starting materials described above, are known in the art. For specific guidance, the reader is referred to Brown, D. J., "The Pyrimidines", in *The Chemistry of Heterocyclyl Compounds,* Volume 16 (Weissberger, A., Ed.), 1962, Interscience Publishers, (A Division of John Wiley & Sons), New York ("Brown I"); Brown, D. J., "The Pyrimidines", in *The Chemistry of Heterocyclyl Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclyl Compounds, Volume 16, Supplement II* (Weissberger, A. and Taylor, E. C., Ed.), 1985, An Interscience Publication (John Wiley & Sons), New York ("Brown III");

Brown, D. J., "The Pyrimidines" in *The Chemistry of Heterocyclyl Compounds*, Volume 52 (Weissberger, A. and Taylor, E. C., Ed.), 1994, John Wiley & Sons, Inc., New York, pp. 1-1509 (Brown IV"); Kenner, G. W. and Todd, A., in *Heterocyclyl Compounds*, Volume 6, (Elderfield, R. C., Ed.), 1957, John Wiley, New York, Chapter 7 (pyrimidines); Paquette, L. A., *Principles of Modern Heterocyclyl Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclyl Chemistry*, 3$^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclyl Chemistry*, 4$^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

| | |
|---|---|
| mL = | milliliter |
| s = | singlet |
| d = | doublet |
| t = | triplet |
| q = | quartet |
| m = | multiplet |
| dd = | doublet of doublets |
| br = | broad |
| nM = | nanomolar |
| µg = | microgram |
| ng = | nanogram |
| MS = | mass spectrum or mass spectrometry |
| LC = | liquid chromatography |
| DMSO = | dimethylsulfoxide |
| µL = | microliter |
| mM = | millimolar |
| rpm = | revolutions per minute |
| LAH = | lithium aluminum hydride |
| HEPES = | N-(2-hydroxyethyl)-piperazine-N'-2-ethanesulfonic acid |
| EGTA = | Ethylene glycol-bis(beta-aminoethyl ether)-N,N,N',N'-tetraacetic acid |
| BRIJ-35 = | polyoxyethyleneglycol dodecyl ether detergent |

Example 1

N2-(3-aminosulfonyl-4-methyl)phenyl-N4-(3-ethylaminosulfonyl-aminomethyl)phenyl-5-methyl-2,4-pyrimidinediamine

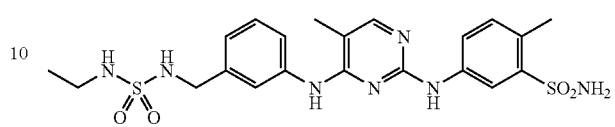

Tert-butyl N-(3-nitrobenzylsulfamoyl)carbamate

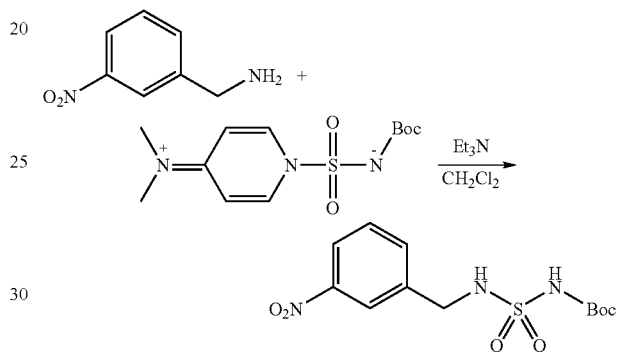

3-Nitrobenzylamine HCl salt (1 g, 5.3 mmol) and 4-Pyridinaminium, 1-[[[(1,1-dimethylethoxy)carbonyl]amino]sulfonyl]-1,4-dihydro-N,N-dimethyl-, inner salt (2.4 g) were dissolved in dichloromethane (20 mL) and triethylamine (2.2 mL). The solution was stirred at ambient temperature for three days. The reaction mixture was diluted with 1N HCl aq. (100 mL) and extracted with ethyl acetate (3×100 mL). The organic solutions were evaporated to give tert-butyl N-(3-nitrobenzylsulfamoyl)carbamate which was not isolated. MS (m/e): 330.11 (MH−).

N-(3-nitrobenzyl)-N'-ethylsulfamide

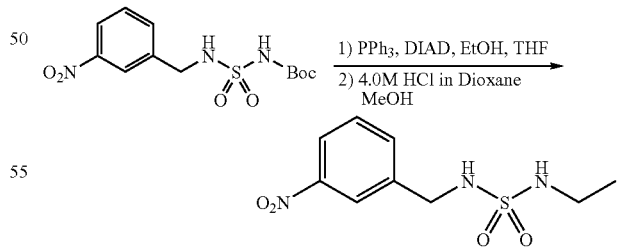

Crude tert-butyl N-(3-nitrobenzylsulfamoyl)carbamate, triphenylphosphine (2 g) and diisopropyl azadicarboxylate (DIAD, 1.6 g) were dissolved in THF (20 mL) and ethanol (0.47 mL). The solution was stirred at ambient temperature overnight. The reaction solution was evaporated to dryness. The residue was dissolved in methanol (10 mL) and treated with 4.0 M HCl in dioxane (10 mL). It was stirred at rt overnight and then evaporated. The residue was diluted with ethyl acetate (100 mL) and washed with NaHCO3 aq. (2×100 mL). The organic solution was evaporated and purified by flash column chromatography (EtOAc/hexane=1/2, 1/1) to give N-(3-nitrobenzyl)-N'-ethylsulfamide. $^1$H NMR (DMSO-d$_6$): δ 1.02 (t, J=7.2 Hz, 3H), 2.82 (p, J=6.9 Hz, 2H), 4.14 (d, J=6.6 Hz, 2H), 6.93 (t, J=5.4 Hz, 1H), 7.54 (t, J=6.3 Hz, 1H), 7.61 (t, J=7.8 Hz, 1H), 7.77 (d, J=7.2 Hz, 1H), 8.10 (d, J=8.1 Hz, 1H), 8.20 (s, 1H); LCMS: purity: 1.2 g, 88.4%; MS (m/e): 260.16 (MH+).

N-(3-nitrobenzyl)-N'-ethylsulfamide was dissolved in methanol (100 mL) and to the solution was added 10% Pd—C. The reaction mixture was reacted under hydrogen atmosphere (~40 psi) for 1 h. The catalyst was filtered off over celite and washed with methanol. The filtrate was evaporated to give N-(3-aminobenzyl)-N'-ethylsulfamide. $^1$H NMR (DMSO-d$_6$): δ 1.03 (t, J=7.2 Hz, 3H), 2.83 (p, J=6.9 Hz, 2H), 3.81 (d, J=6.3 Hz, 2H), 5.02 (s, 2H), 6.41 (t, J=7.8 Hz, 2H), 6.51 (s, 1H), 6.76 (t, J=5.7 Hz, 1H), 6.91 (t, J=7.5 Hz, 1H), 7.16 (t, J=6.3 Hz, 1H).

2-Chloro-N4-(3-ethylaminosulfonylaminomethyl)phenyl-5-methyl-4-pyrimidineamine

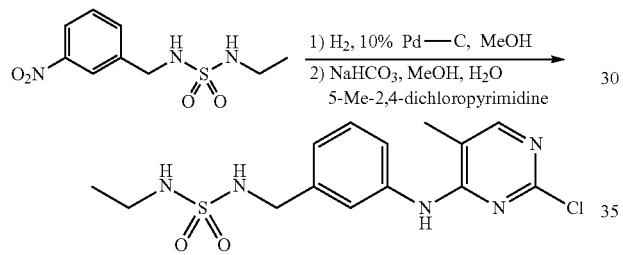

N-(3-Aminobenzyl)-N'-ethylsulfamide (1.2 g, 4.7 mmol, 2,4-dichloro-5-methylpyrimidine (1.5 g, 9.2 mmol) and NaHCO3 (1 g) were dissolved in methanol (10 mL) and water (1 mL). The reaction solution was stirred at 60° C. overnight. The reaction mixture was diluted with 1N HCl aq. (100 mL) and extracted with ethyl acetate (2×100 mL). The organic solutions were evaporated and purified by flash column chromatography (EtOAc/hexanes=1/4, 1/2, 1/1, EtOAc) to give 2-chloro-N4-(3-ethylaminosulfonylaminomethyl)phenyl-5-methyl-4-pyrimidineamine. LCMS: purity: 91.88%; MS (m/e): 356.46 (MH+).

N2-(3-Aminosulfonyl-4-methyl)phenyl-N4-(3-ethylaminosulfonylaminomethyl)phenyl-5-methyl-2,4-pyrimidinediamine

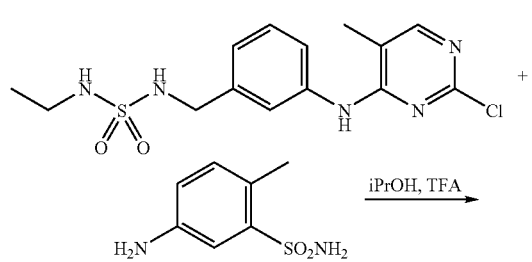

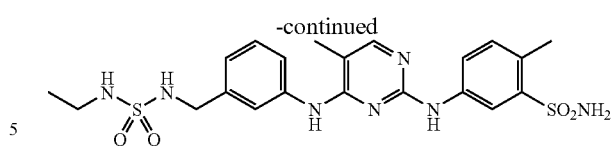

2-Chloro-N4-(3-ethylaminosulfonylaminomethyl)phenyl-5-methyl-4-pyrimidineamine (50 mg) and (3-aminosulfonyl-4-methyl)aniline (50 mg) were suspended in isopropanol (1 mL) and TFA (5 drops). The solution was heated at 100° C. overnight, then cooled to room temperature. The solution was evaporated and purified by HPLC to give N2-(3-aminosulfonyl-4-methyl)phenyl-N4-(3-ethylaminosulfonylaminomethyl)phenyl-5-methyl-2,4-pyrimidinediamine. $^1$H NMR (DMSO-d$_6$): δ 1.02 (t, J=7.2 Hz, 3H), 2.16 (s, 3H), 2.52 (s, 3H), 2.83 (m, J=6.3 Hz, 2H), 4.00 (d, J=6.3 Hz, 2H), 6.84 (t, 1H), 7.19 (m, 2H), 7.34 (m, 4H), 7.43 (s, 1H), 7.49 (d, 1H), 7.74 (m, 2H), 7.86 (s, 1H), 9.58 (br, 1H), 10.11 (br, 1H); LCMS: purity: 97.72%; MS (m/e): 506.25 (MH$^+$).

The following examples were made using methods analogous to the example above:

I-1: N2-(3-Aminosulfonylphenyl)-5-chloro-N4-[4-[(N,N-dimethylsulfamoylamino)methyl]phenyl]-2,4-pyrimidinediamine LCMS: Purity: 99%; MS (m/e): 513 (MH$^+$). $^1$H NMR (DMSO-d6): δ9.98 (s, 1H), 9.29 (s, 1H), 8.23 (s, 1H), 7.93-7.89 (m, 2H), 7.71 (t, 1H, J=6.4 Hz), 7.59 (d, 2H, J=8.2 Hz), 7.40-7.30 (m, 6H), 4.09 (s, 2H), 2.63 (s, H).

I-2: N2-(4-Aminosulfonylphenyl)-5-chloro-N4-[4-[(N,N-dimethylsulfamoylamino)methyl]phenyl]-2,4-pyrimidinediamine LCMS: Purity: 99%; MS (m/e): 513 (MH$^+$). $^1$H NMR (DMSO-d6): δ10.91 (s, 1H), 9.18 (s, 1H), 8.23 (s, 1H), 7.75-7.72 (app m, 3H, J=8.8 Hz), 7.59 (m, 4H), 7.34 (d, 2H, J=8.5 Hz), 7.15 (br s, 2H), 4.11 (m, 2H), 2.64 (s, 6H).

I-3: N2-(3-Aminosulfonylphenyl)-N-4-[4-[(N,N-dimethylsulfamoylamino)methyl]phenyl]-5-methyl-2,4-pyrimidinediamine LCMS: Purity: 99%; MS (m/e): 492 (MH$^+$). $^1$H NMR (DMSO-d6): δ10.63 (s, 1H), 9.77 (s, 1H), 7.93 (s, 1H), 7.82 (d, 1H, J=8.5 Hz), 7.72 (t, 1H, J=6.7 Hz), 7.65 (s, 1H), 7.51-7.48 (m, 3H), 7.42-7.34 (m, 5H), 4.12 (d, 2H, J=6.7 Hz), 2.64 (s, 6H), 2.16 (s, 3H).

I-4: N2-(4-Aminosulfonylphenyl)-N4-[4-[(N,N-dimethylsulfamoylamino)methyl]phenyl]-5-methyl-2,4-pyrimidinediamine LCMS: Purity: 99%; MS (m/e): 492 (MH$^+$). $^1$H NMR (DMSO-d6): δ10.60 (s, 1H), 9.65 (s, 1H), 7.95 (s, 1H), 7.72 (t, 1H, J=6.2 Hz), 7.66-7.51 (m, 6H), 7.38 (d, 2H, J=8.5 Hz), 7.24 (s, 2H), 4.14 (d, 2H, J=6.2 Hz), 2.64 (s, 6H), 2.17 (s, 3H).

I-5: N2-(3-Aminosulfonylphenyl)-5-chloro-N4-[4-[(N-ethylsulfamoylamino)methyl]phenyl]-2,4-pyrimidinediamine LCMS: Purity: 99%; MS (m/e): 513 (MN). $^1$H NMR (DMSO-d6): δ9.72 (s, 1H), 9.00 (s, 1H), 8.18 (s, 1H), 7.94 (s, 1H), 7.74 (br s, 2H), 7.61 (d, 2H, J=8.5 Hz), 7.36-7.27 (m, 7H), 3.99 (br s, 2H), 2.85 (qt, 2H, J=7.3 Hz), 1.02 (t, 3H, J=7.3 Hz).

I-6: N2-(4-Aminosulfonylphenyl)-5-chloro-N4-[4-[(N-ethylsulfamoylamino)methyl]phenyl]-2,4-pyrimidinediamine LCMS: Purity: 97%; MS (m/e): 513 (MH$^+$). $^1$H NMR (DMSO-d6): δ9.78 (s, 1H), 9.05 (s, 1H), 8.20 (s, 1H), 7.76 (d, 2H, J=8.8 Hz), 7.60 (d, 4H, J=8.8 Hz), 7.33 (app d, 3H, J=8.8 Hz), 6.73 (br s, 1H), 4.01 (s, 2H), 2.85 (qt, 2H, J=7.3 Hz), 1.02 (t, 3H, J=7.3 Hz).

I-7: N2-(3-Aminosulfonylphenyl)-N4-[4-[(N-ethylsulfamoylamino)methyl]phenyl]-5-methyl-2,4-pyrimidinediamine LCMS: Purity: 97%; MS (m/e): 492 (MH$^+$). $^1$H NMR (DMSO-d6): δ10.59 (s, 1H), 9.76 (s, 1H), 7.92 (s, 1H), 7.82 (d, 1H, J=8.2 Hz), 7.65 (s, 1H), 7.49-7.42 (m, 3H), 7.38-7.33 (m, 6H), 6.89 (s, 1H), 4.01 (d, 2H, J=5.2 Hz), 2.84 (app m, 2H), 2.16 (s, 3H), 1.03 (t, 3H, J=7.3 Hz).

I-8: N2-(4-Aminosulfonylphenyl)-N4-[4-[(N-ethylsulfamoylamino)methyl]phenyl]-5-methyl-2,4-pyrimidinediamine LCMS: Purity: 99%; MS (m/e): 492 (MH$^+$). $^1$H NMR (DMSO-d6): δ10.69 (s, 1H), 9.77 (s, 1H), 7.95 (s, 1H), 7.65 (d, 2H, J=9.1 Hz), 7.5 (d, 2H, J=9.1 Hz), 7.51 (d, 2H, J=8.8 Hz), 7.37 (app d, 3H, J=8.8 Hz), 7.25 (s, 2H), 6.88 (s, 1H), 4.02 (d, 2H, J=5.2 Hz), 2.86 (app qt, 2H, J=7.3 Hz), 1.02 (t, 3H, J=7.3 Hz).

I-9: N2-(3-Aminosulfonylphenyl)-5-chloro-N4-[3-[(N-ethylsulfamoylamino)methyl]phenyl]-2,4-pyrimidinediamine LCMS: Purity: 97%; MS (m/e): 513 (MH$^+$). $^1$H NMR (DMSO-d6): δ9.82 (s, 1H), 9.20 (s, 1H), 8.22 (s, 1H), 7.91 (m, 2H), 7.59-7.54 (m, 2H), 7.39-7.03 (m, 5H), 7.16 (d, 1H, J=7.3 Hz), 4.00 (s, 2H), 2.82 (qt, 2H, J=7.3 Hz), 1.02 (t, 3H, J=7.3 Hz).

I-10: N2-(4-Aminosulfonylphenyl)-5-chloro-N4-[3-[(N-ethylsulfamoylamino)methyl]phenyl]-2,4-pyrimidinediamine LCMS: Purity: 90%; MS (m/e): 513 (MH$^+$). $^1$H NMR (DMSO-d6): δ9.83 (s, 1H), 9.19 (s, 1H), 8.22 (s, 1H), 7.73-7.70 (m, 2H), 7.58-7.51 (m, 4H), 7.35-7.00 (m, 2H), 7.19-7.13 (m, 2H), 4.02 (s, 2H), 2.82 (qt, 2H, J=7.3 Hz), 1.02 (m, 3H).

I-11: N2-(3-Aminosulfonylphenyl)-N4-[3-[(N-ethylsulfamoylamino)methyl]phenyl]-5-methyl-2,4-pyrimidinediamine LCMS: Purity: 99%; MS (m/e): 492 (MH$^+$). $^1$H NMR (DMSO-d6): δ10.50 (s, 1H), 9.76 (s, 1H), 7.93 (s, 1H), 7.82 (d, 1H, J=8.5 Hz), 7.65 (s, 1H), 7.50-7.48 (m, 2H), 7.42-7.33 (m, 6H), 7.21 (d, 1H, J=7.6 Hz), 6.85-6.84 (m, 1H), 3.99 (d, 2H, J=6.2 Hz), 2.81-2.80 (m, 2H), 2.16 (s, 3H), 1.02 (t, 3H, J=7.3 Hz).

I-12: N2-(4-Aminosulfonylphenyl)-N4-[3-[(N-ethylsulfamoylamino)methyl]phenyl]-5-methyl-2,4-pyrimidinediamine LCMS: Purity: 90%; MS (m/e): 492 (MH$^+$). $^1$H NMR (DMSO-d6): δ9.41 (s, 1H), 8.51 (s, 1H), 7.93 (s, 1H), 7.81-7.78 (d, 2H, J=9.1 Hz), 7.64 (d, 1H, J=8.2 Hz), 7.58-7.54 (m, 3H), 7.35-7.28 (m, 2H), 7.09-7.07 (m, 3H), 6.82 (t, 1H, J=5.8 Hz), 4.01 (d, 2H, J=6.4 Hz), 2.82 (d qt, 2H, J=5.6 and 7.3 Hz), 2.12 (s, 3H), 1.01 (t, 3H, J=7.3 Hz).

I-13: N2-(3-Aminosulfonylphenyl)-N4-[3-[(N-ethylsulfamoylamino)methyl]phenyl]-5-fluoro-2,4-pyrimidinediamine LCMS: Purity: 92%; MS (m/e): 496 (MH$^+$). $^1$H NMR (DMSO-d6): δ9.78 (s, 1H), 8.19 (d, 1H, J=4.1 Hz), 8.00 (s, 1H), 7.93-7.90 (m, 1H), 7.73 (d, 1H, J=7.6 Hz), 7.64 (s, 1H), 7.41-7.28 (m, 5H), 7.09 (d, 1H, J=6.7 Hz), 3.99 (s, 2H), 2.83 (app qt, 2H, J=7.3 Hz), 1.02 (t, 3H, J=7.3 Hz).

I-14: N2-(4-Aminosulfonylphenyl)-N4-[3-[(N-ethylsulfamoylamino)methyl]phenyl]-5-fluoro-2,4-pyrimidinediamine LCMS: Purity: 97%; MS (m/e): 496 (MH$^+$). $^1$H NMR (DMSO-d6): δ9.71 (s, 1H), 9.67 (s, 1H), 8.18 (d, 1H, J=3.8 Hz), 7.80-7.71 (m, 3H), 7.62 (app d, 3H, J=8.8 Hz), 7.35-7.29 (m, 1H), 7.13-7.01 (m, 3H), 4.00 (s, 2H), 2.83 (qt, 2H, J=7.3 Hz), 1.02 (t, 3H, J=7.3 Hz).

I-15: N2-(3-Aminosulfonylphenyl)-5-chloro-N4-[4-[(N-ethylsulfamoylamino)methyl]-2-methylphenyl]-2,4-pyrimidinediamine LCMS: Purity: 99%; MS (m/e): 527 (MN). $^1$H NMR (DMSO-d6): δ9.49 (s, 1H), 8.73 (s, 1H), 7.86 (s, 1H), 7.75 (d, 1H, J=8.2 Hz), 7.34 (t, 1H, J=6.7 Hz), 7.26-7.12 (m, 7H), 6.89 (t, 1H, J=5.6 Hz), 4.02 (d, 2H, J=6.4 Hz), 2.88 (d qt, 2H, J=5.6 and 7.3 Hz), 2.14 (s, 3H), 1.06 (t, 3H, J=7.3 Hz).

I-16: N2-(4-Aminosulfonylphenyl)-5-chloro-N4-[4-[(N-ethylsulfamoylamino)methyl]-2-methylphenyl]-2,4-pyrimidinediamine LCMS: Purity: 99%; MS (m/e): 527 (MH$^+$). $^1$H NMR (DMSO-d6): δ9.58 (s, 1H), 8.80 (s, 1H0, 7.59 (d, 2H, J=8.5 Hz), 7.44 (d, 2H, J=8.5 Hz), 7.34 (t, 1H, J=5.4 Hz), 7.27-7.20 (m, 3H), 7.05 (s, 2H), 6.87 (t, 1H, J=6.2 Hz), 4.03 (d, 2H, J=6.4 Hz), 2.86 (m, 2H, J=7.0 Hz), 2.15 (s, 3H), 11.05 (t, 3H, J=7.3 Hz).

I-17: N2-(4-Aminosulfonyl-3,5-dimethylphenyl)-5-chloro-N4-[4-[(N-ethylsulfamoylamino) methyl]-2-methylphenyl]-2,4-pyrimidinediamine LCMS: Purity: 99%; MS (m/e): 555 (MH$^+$). $^1$H NMR (DMSO-d6): δ9.38 (s, 1H), 8.77 (s, 1H), 7.33 (t, 1H, J=5.2 Hz), 7.25-7.19 (m, 5H), 6.95 (s, 2H), 6.89 (t, 1H, J=5.8 Hz), 3.98 (d, 2H, J=6.4 Hz), 2.87 (m, 2H), 2.27 (s, 6H), 2.14 (s, 3H), 1.05 (t, 2H, J=7.3 Hz).

I-18: N2-(3-Aminosulfonylphenyl)-5-chloro-N4-[4-[(N-cyclopropylsulfamoylamino)methyl]phenyl]-2,4-pyrimidinediamine LCMS: Purity: 99%; MS (m/e): 525 (MH$^+$). $^1$H NMR (DMSO-d6): δ9.61 (s, 1H), 8.86 (s, 1H), 8.15 9s, 1H), 7.98 (s, 2H), 7.62 (d, 2H, J=8.5 Hz), 7.46 (t, 1H, J=5.4 Hz), 7.33-7.26 (m, 7H), 4.02 (d, 2H, J=6.4 Hz), 2.31 (m, 1H), 0.54-0.51 (m, 4H).

I-19: N2-(4-Aminosulfonylphenyl)-5-chloro-N4-[4-[(N-cyclopropylsulfamoylamino)methyl]phenyl]-2,4-pyrimidinediamine LCMS: Purity: 99%; MS (m/e): 525 (MH+).

I-20: N2-(4-Aminosulfonyl-3,5-dimethylphenyl)-5-chloro-N4-[4-[(N-cyclopropylsulfamoyl-amino)methyl]phenyl]-2,4-pyrimidinediamine LCMS: Purity: 99%; MS (m/e): 553 (MH+). $^1$H NMR (DMSO-d6): δ9.48 (s, 1H), 8.91 (s, 1H0, 8.18 (s, 1H), 7.76-7.42 (m, 3H), 7.46 (t, 1H, J=5.4 Hz), 7.33-7.30 (m, 4H), 7.11 (s, 2H), 4.00 (d, 2H, J=6.4 Hz), 2.47 (s, 6H), 2.31-2.28 (m, 1H), 0.54-0.52 (m, 4H).

I-21: N2-(3-Aminosulfonylphenyl)-N4-[4-[(N-cyclopropylsulfamoylamino)methyl]phenyl]-5-methyl-2,4-pyrimidinediamine LCMS: Purity: 99%; MS (m/e): 504 (MN). $^1$H NMR (DMSO-d6): δ9.28 (s, 1H), 8.28 (s, 1H), 8.07 (s, 1H), 8.01 (d, 1H, J=8.5 Hz), 7.89 (s, 1H), 7.68 (d, 2H, J=9.1 Hz), 7.43-7.22 (m, 8H), 4.00 (d, 2H, J=6.4 Hz), 2.31-2.30 (m, 1H), 2.10 (s, 3H), 0.54-0.52 (m, 4H).

I-22: N2-(4-Aminosulfonylphenyl)-N4-[4-[(N-cyclopropylsulfamoylamino)methyl]phenyl]-5-methyl-2,4-pyrimidinediamine LCMS: Purity: 99%; MS (m/e): 504 (MH+). $^1$H NMR (DMSO-d6): δ9.38 (s, 1H), 8.35 (s, 1H), 7.92 (s, 1H), 7.84 (d, 2H, J=8.8 Hz), 7.65 (d, 2H, J=8.8 Hz), 7.62 (d, 2H, J=8.8 Hz), 7.42 (t, 1H, J=6.4 Hz), 7.32-7.29 (m, 3H), 7.07 (s, 2H), 4.03 (d, 2H, J=6.4 Hz), 2.31-2.30 (m, 1H), 2.11 (s, 3H), 0.54-0.52 (m, 4H).

I-23: N2-(4-Aminosulfonyl-3,5-dimethylphenyl)-N4-[4-[(N-cyclopropylsulfamoylamino) methyl]phenyl]-5-methyl-2,4-pyrimidinediamine LCMS: Purity: 99%; MS (m/e): 532 (MN). $^1$H NMR (DMSO-d6): δ9.16 (s, 1H), 8.32 (s, 1H), 7.90 (s, 1H), 7.62 (d, 2H, J=8.8 Hz), 7.44 (s, 2H), 7.38 (t, 1H, J=6.4 Hz), 7.30-7.28 (m, 2H), 6.97 (s, 2H), 4.00 (d, 2H, J=6.4 Hz), 2.42 (s, 6H), 2.31-2.30 (m, 1H), 2.10 (s, 3H), 0.54-0.50 (m, 4H).

I-24: N2-(3-Aminosulfonylphenyl)-5-chloro-N4-[4-[(N-cyclopropylsulfamoylamino)methyl]-2-methylphenyl]-2,4-pyrimidinediamine LCMS: Purity: 99%; MS (m/e): 539 (MH+). $^1$H NMR (DMSO-d6): δ9.49 (s, 1H), 8.73 (s, 1H), 8.09 (s, 1H), 7.86 (s, 1H), 7.75 (d, 1H, J=8.5 Hz), 7.51 (t, 1H, J=6.7 Hz), 7.33 (s, 1H), 7.25-7.12 (m, 7H), 4.04 (d, 2H, J=6.4 Hz), 2.36-2.31 (m, 1H), 2.14 (s, 3H), 0.59-0.54 (m, 4H).

I-25: N2-(4-Aminosulfonylphenyl)-5-chloro-N4-[4-[(N-cyclopropylsulfamoylamino)methyl]-2-methylphenyl]-2,4-pyrimidinediamine LCMS: Purity: 99%; MS (m/e): 539 (MH+). $^1$H NMR (DMSO-d6): δ9.56 (s, 1H), 8.80 (s, 1H), 8.13 (s, 1H), 7.58 (d, 2H, J=8.5 Hz), 7.49 (t, 1H, J=6.7 Hz), 7.45 (d, 2H, J=8.8 Hz), 7.32-7.21 (m, 4H), 7.06 (s, 1H), 4.06 (d, 2H, J=6.4 Hz), 2.32-2.31 (m, 1H), 2.15 (s, 3H), 0.58-0.51 (m, 4H).

I-26: N2-(4-Aminosulfonyl-3,5-dimethylphenyl)-5-chloro-N4-[4-[(N-cyclopropylsulfamoyl-amino)methyl]-2-methylphenyl]-2,4-pyrimidinediamine LCMS: Purity: 98%; MS (m/e): 566 (MH+). $^1$H NMR (DMSO-d6): δ9.38 (s, 1H), 8.77 (s, 1H), 8.10 (s, 1H), 7.46 (t, 1H, J=6.7 Hz), 7.34 (s, 1H), 7.26-7.20 (m, 5H), 6.95 (s, 2H), 4.00 (d, 2H, J=6.4 Hz), 2.31-2.300 (m, 1H), 2.27 (s, 6H), 2.14 (s, 3H), 0.55-0.51 (m, 4H).

I-27: N4-[3-(N-ethyl-N-propionyl)aminosulfonyl-(N-propionyl)aminomethyl]phenyl-5-methyl-N2-(3-propionylaminosulfonyl)phenyl-2,4-pyrimidinediamin LCMS: purity: 90.67%; MS (m/e): 660.42 (MH+). $^1$H NMR (DMSO-d$_6$): δ 0.88 (t, J=7.5 Hz, 3H), 0.92 (t, J=7.5 Hz, 3H), 0.98 (t, J=7.2 Hz, 3H), 1.22 (t, J=7.5 Hz, 3H), 2.13 (s, 3H), 2.20 (q, J=7.2 Hz, 2H), 2.56-2.64 (m, 4H), 3.83 (q, J=7.8 Hz, 2H), 5.05 (s, 2H), 6.98 (d, J=8.1 Hz, 1H), 7.34 (m, 3H), 7.65 (m, 2H), 7.92 (s, 1H), 8.08 (d, 1H), 8.19 (s, 1H), 8.43 (s, 1H), 9.20 (s, 1H), 11.95 (s, 1H).

I-28: N4-[3-(N-ethyl-N-propionyl)aminosulfonyl-(N-propionyl)aminomethyl]phenyl-5-methyl-N2-(3-propionylaminosulfonyl)phenyl-2,4-pyrimidinediamine Sodium Salt LCMS: purity: 87.50%; MS (m/e): 660.42 (MH+). $^1$H NMR (DMSO-d$_6$): δ 0.83 (t, J=7.5 Hz, 3H), 0.92 (t, J=7.2 Hz, 3H), 0.99 (t, J=7.2 Hz, 3H), 1.23 (t, J=6.9 Hz, 3H), 1.88 (q, J=7.5 Hz, 2H), 2.11 (s, 3H), 2.56-2.64 (m, 4H), 3.82 (q, J=7.5 Hz, 2H), 5.05 (s, 2H), 6.94 (d, J=6.9 Hz, 1H), 7.11 (t, J=7.5 Hz, 1H), 7.20 (d, J=7.2 Hz, 1H), 7.31 (t, J=7.8 Hz, 1H), 7.66 (d, J=6.6 Hz, 1H), 7.77 (s, 1H), 7.83 (m, 2H), 7.89 (s, 1H), 8.31 (s, 1H), 8.84 (s, 1H).

I-29: N2-(3-aminosulfonyl-4-methyl)phenyl-N4-(3-ethylaminosulfonylaminomethyl)phenyl-5-methyl-2,4-pyrimidinediamine LCMS: purity: 97.72%; MS (m/e): 506.25 (MH+). $^1$H NMR (DMSO-d$_6$): δ 1.02 (t, J=7.2 Hz, 3H), 2.16 (s, 3H), 2.52 (s, 3H), 2.83 (m, J=6.3 Hz, 2H), 4.00 (d, J=6.3 Hz, 2H), 6.84 (t, 1H), 7.19 (m, 2H), 7.34 (m, 4H), 7.43 (s, 1H), 7.49 (d, 1H), 7.74 (m, 2H), 7.86 (s, 1H), 9.58 (br, 1H), 10.11 (br, 1H).

I-30: N2-(3-aminosulfonyl)phenyl-N4-(3-N,N-dimethylaminosulfonylaminomethyl)-5-methyl-2,4-pyrimidinediamine LCMS: purity: 96.46%; MS (m/e): 492.29 (MH+). $^1$H NMR (DMSO-d$_6$): δ 2.15 (s, 3H), 2.62 (s, 6H), 4.09 (d, J=6.3 Hz, 2H), 7.15 (d, 1H), 7.31 (s, 2H), 7.35 (m, 2H), 7.42 (d, 1H), 7.49 (s, 1H), 7.55 (d, 1H), 7.69 (t, 1H), 7.80 (s, 1H), 7.89 (m, 2H).

I-31: N2-(4-aminosulfonyl)phenyl-N4-(3-N,N-dimethylaminosulfonylaminomethyl)-5-methyl-2,4-pyrimidinediamine LCMS: purity: 92.92%; MS (m/e): 492.30 (MH+). $^1$H NMR (DMSO-d$_6$): δ 2.15 (s, 3H), 2.62 (s, 6H), 4.10 (d, 2H), 7.18 (br, 3H), 7.36 (t, J=7.8 Hz, 1H), 7.48 (s, 1H), 7.60 (m, 3H), 7.69 (m, 3H), 7.92 (s, 1H).

I-32: N2-(3-aminosulfonyl-4-methyl)phenyl-N4-(3-N,N-dimethylaminosulfonylamino-methyl)-5-methyl-2,4-pyrimidinediamine LCMS: purity: 92.48%; MS (m/e): 506.29 (MH+). $^1$H NMR (DMSO-d$_6$): δ 2.15 (s, 3H), 2.62 (s, 6H), 4.09 (d, J=5.4 Hz, 2H), 7.16 (d, J=8.4 Hz, 2H), 7.31 (m, 3H), 7.48 (s, 1H), 7.56 (d, 1H), 7.69 (m, 1H), 7.71 (m, 1H), 7.80 (br, 1H), 7.85 (s, 1H).

II-1: N2-(3-aminosulfonyl-4-methyl)phenyl-N4-(2-N,N-dimethylaminosulfonyl-1,2,3,4-tetrahydroisoquinolin-7-yl)-5-fluoro-2,4-pyrimidinediamine $C_{22}H_{26}FN_7O_4S_2$. MS (ESI) m/z 535.92 (M+1)$^+$. $^1$H NMR (300 MHz, CD$_3$SOCD$_3$) δ ppm: 2.49 (s, 6H, 2XNCH$_3$), 2.74-2.82 (m, 7H, CH$_3$ and 2CH$_2$), 4.37 (s, 2H, CH$_2$), 7.12 (d, J=10.0 Hz, 1H, ArH), 7.20 (d, J=10.0 Hz, 1H, ArH), 7.24 (s, 2H, NH$_2$), 7.51 (m, 1H, ArH), 7.71 (s, 1H, ArH), 7.93 (d, J=6.7 Hz, 1H, ArH), 8.05 (s, 1H, ArH), 8.08 (d, J=6.7 Hz, 1H, ArH), 9.35 (s, 1H, NH), 9.45 (s, 1H, NH).

II-2: N2-(3-aminosulfonyl-4-methyl)phenyl-N4-(2-N,N-dimethylaminosulfonyl-2,3-dihydro-1H-isoindol-5-yl)-5-fluoro-2,4-pyrimidinediamine $C_{21}H_{24}FN_7O_4S_2$. MS (ESI) m/z 550.94 (M+1)$^+$. $^1$H NMR (300 MHz, CD$_3$SOCD$_3$) δ ppm: 2.48 (s, 6H, 2XNCH$_3$), 2.81 (s, CH$_3$), 4.56 (s, 2H, CH$_2$), 7.18 (m, 1H, ArH), 7.21 (m, 1H, ArH), 7.26 (s, 2H, NH$_2$), 7.59 (m, 1H, ArH), 7.83 (m, 2H, 2ArH), 8.02 (m, 1H, ArH), 8.12 (d, J=6.7 Hz, 1H, ArH), 9.48 (s, 1H, NH), 9.56 (s, 1H, NH).

II-3: N2-(4-aminosulfonyl)phenyl-N4-(2-N,N-dimethylaminosulfonyl-2,3-dihydro-1H-isoindol-5-yl)-5-methyl-2,4-pyrimidinediamine LCMS: purity: 77.64%; MS (m/e): 504.26 (MH+). $^1$H NMR (DMSO-d$_6$): δ 2.12 (s, 3H), 2.81 (s, 6H), 4.60 (s, 4H), 7.08 (br, 2H), 7.28 (d, J=7.8 Hz, 1H), 7.57 (d, J=8.7 Hz, 3H), 7.68 (s, 1H), 7.80 (d, J=8.1 Hz, 2H), 7.93 (s, 1H), 8.45 (s, 1H), 9.38 (s, 1H).

II-4: N2-(3-aminosulfonyl)phenyl-N4-(2-N,N-dimethylaminosulfonyl-2,3-dihydro-1H-isoindol-5-yl)-5-methyl-2,4-pyrimidinediamine LCMS: purity: 87.83%; MS (m/e): 504.53 (MH+). $^1$H NMR (DMSO-d$_6$): δ 2.11 (s, 3H), 2.81 (s, 6H), 4.58 (s, 4H), 7.24 (br, 2H), 7.29 (m, 3H), 7.57 (d, J=9.6 Hz, 1H), 7.77 (s, 1H), 7.90 (s, 1H), 7.99 (d, J=7.2 Hz, 1H), 8.05 (s, 1H), 8.37 (s, 1H), 9.27 (s, 1H).

II-5: N2-(3-aminosulfonyl-4-methyl)phenyl-N4-(2-N,N-dimethylaminosulfonyl-2,3-dihydro-1H-isoindol-5-yl)-5-methyl-2,4-pyrimidinediamine LCMS: purity: 92.70%; MS (m/e): 518.35 (MH+). $^1$H NMR (DMSO-d$_6$): δ 2.15 (s, 3H), 2.53 (s, 3H), 2.80 (s, 6H), 4.53 (s, 2H), 4.59 (s, 2H), 7.17 (d, J=9.0 Hz, 1H), 7.31 (m, 3H), 7.43 (d, 1H), 7.57 (s, 1H), 7.68 (d, 1H), 7.79 (s, 1H), 7.86 (s, 1H).

Example 2

Cell Titer-Glo, Human Primary T Cell, IL2

Materials and Reagents: Dimethyl Sulfoxide (DMSO) (Sigma-Aldrich, Cat#D2650) was used as a control. The following reagents were used: Ficoll Hypaque (Amersham Pharmacia, Cat#17-1440-03), Anti-Human CD3 (BD Pharmingen, Cat#555336), Anti-Human CD28 (Immunotech, Cat#IM1376), Yssel's Media (Gemini Bio-products, Cat#400-103), RPMI 1640 (Cellgro, Cat#10-040-CM), Fetal Bovine Serum (JRH, Cat#12106-500M), and Anti-Human IL-2 (R& D Systems, Cat#202-IL).

Human primary T-cells were isolated and cultured according to the following procedure. Whole blood was obtained from a healthy volunteer, mixed 1:1 with PBS, layered on to Ficoll Hypaque in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium containing 40 U/mL IL-2 and seeded into a flask pre-coated with 1 mg/mL anti-CD3 and 5 mg/mL anti-CD28. The primary T-cells were stimulated for 3-4 days, then transferred to a fresh flask and maintained in RPMI with 10% FBS and 40 U/mL IL-2.

Primary T-cells were starved of IL-2 overnight and resuspended in Yssel's medium at 2×10$^6$ cells/mL. 50 μL of cell suspension containing 80 U/mL IL-2 was added to each well of a flat bottom 96 well black plate. For the unstimulated control, IL-2 was omitted from the last column on the plate. Compound was serially diluted in DMSO from 5 mM in 3-fold dilutions, and then diluted 1:250 in Yssel's medium. 50 μL of 2× compound was added per well in duplicate and the cells were allowed to proliferate for 72 hours at 37° C.

Proliferation was measured using Cell Titer-Glo. The substrate was thawed and allowed to come to room temperature. After mixing the Cell Titer-Glo reagent and diluent together, 100 μL was added to each well. The plates were mixed on an orbital shaker for two minutes to induce lysis and incubated at room temperature for an additional ten minutes to allow the signal to equilibrate. The Luminescence was read on the Wallac Plate Reader (Wallac Victor2 1420 Multilabel Counter).

Compounds tested in the assay described in Example 2, each having an IC$_{50}$ less than 0.5 μM, were I-1 through I-13, I-15, I-17 through I-21, and I-23 through I-24.

What is claimed is:
1. A compound of formula I:

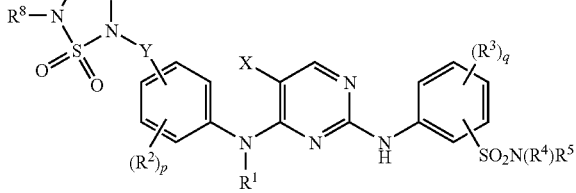

wherein:
p is 0, 1, 2, or 3;
q is 0, 1, 2, or 3;
X is hydrogen, alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl;

Y is a straight or branched chain $C_{1-6}$ alkylene group, cycloalkylene or substituted cycloalkylene;

$R^1$ is hydrogen, alkyl, substituted alkyl, cycloalkyl or substituted cycloalkyl;

each $R^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N(R⁴)R⁵, nitro or halo;

each $R^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;

each $R^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or $M^+$, wherein $M^+$ is $K^+$, $Na^+$, $Li^+$ or $^+N(R^9)_4$, wherein each $R^9$ independently is hydrogen or alkyl, and the nitrogen immediately adjacent to $R^5$ is anionic; or $R^4$ and $R^5$ together with the intervening atom or atoms bound thereto, form a heterocyclyl or substituted heterocyclyl group;

each $R^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;

$R^6$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or $R^6$ is a straight or branched chain $C_{1-6}$ alkylene group, cycloalkylene or substituted cycloalkylene, linking the nitrogen bearing $R^6$ and the ring bearing Y $R^7$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

$R^8$ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or $R^7$ and $R^8$ together, with nitrogen to which they are bound, form a heterocyclyl or substituted heterocyclyl group;

wherein at least one of $R^7$ and $R^8$ is non-hydrogen; and each of $R^6$, $R^7$, and $R^8$ optionally are $M^+$, wherein $M^+$ is $K^+$, $Na^+$, $Li^+$ or $^+N(R^9)_4$, wherein each $R^9$ independently is hydrogen or alkyl, and the nitrogen bearing $M^+$ is anionic.

2. The compound of claim 1, wherein $R^1$ is hydrogen.

3. The compound of claim 2, wherein X is alkyl, substituted alkyl or halo.

4. The compound of claim 1, wherein $R^4$ is hydrogen and $R^5$ is hydrogen.

5. The compound of claim 1, wherein Y is methylene.

6. The compound of claim 1, wherein $R^6$ is hydrogen, $R^7$ is $C_{1-3}$ alkyl and $R^8$ is $C_{1-3}$ alkyl.

7. The compound of claim 1, wherein each of $R^2$ and $R^3$, independently, is lower alkyl or lower alkoxy.

8. The compound of claim 1, according to Formula II:

wherein p is 0, 1, 2, or 3;

q is 0, 1, 2, or 3;

X is hydrogen, alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl;

Y is a straight or branched chain $C_{1-6}$ alkylene group, cycloalkylene or substituted cycloalkylene;

$R^1$ is hydrogen, alkyl, substituted alkyl, cycloalkyl or substituted cycloalkyl;

each $R^2$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, —C(O)N(R⁴)R⁵, nitro or halo;

each $R^3$ independently is alkyl, substituted alkyl, alkoxy, substituted alkoxy, amino, substituted amino, aryl, substituted aryl, aryloxy, substituted aryloxy, cyano, cycloalkyl, substituted cycloalkyl, cycloalkoxy, substituted cycloalkoxy, heteroaryl, substituted heteroaryl, heteroaryloxy, substituted heteroaryloxy, heterocyclyl, substituted heterocyclyl, heterocyclyloxy, substituted heterocyclyloxy, aminoacyl, aminoacyloxy, carboxyl, carboxyl ester, carbonate ester, nitro or halo;

each $R^4$ independently is hydrogen, alkyl, substituted alkyl, cycloalkyl, substituted cycloalkyl, heterocyclyl, substituted heterocyclyl, carboxyl, carboxyl ester, aryl, substituted aryl, heteroaryl, substituted heteroaryl, acyl or $M^+$, wherein $M^+$ is $K^+$, $Na^+$, $Li^+$ or $^+N(R^9)_4$, wherein each $R^9$ independently is hydrogen or alkyl, and the nitrogen immediately adjacent to $R^5$ is anionic; or $R^4$ and $R^5$ together with the intervening atom or atoms bound thereto, form a heterocyclyl or substituted heterocyclyl group;

each $R^5$ independently is hydrogen, alkyl, substituted alkyl, amino, cycloalkyl, substituted cycloalkyl, heterocyclyl, substituted heterocyclyl, aryl, substituted aryl, heteroaryl, substituted heteroaryl, carboxyl, carboxyl ester or acyl;

R⁷ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;

R⁸ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or R⁷ and R⁸ together, with nitrogen to which they are bound, form a heterocyclyl or substituted heterocyclyl group;

R¹⁰ is a straight or branched chain $C_{1-6}$ alkylene group, cycloalkylene or substituted cycloalkylene; and each of R⁷ and R⁸ optionally are M⁺, wherein M⁺ is K⁺, Na⁺, Li⁺ or ⁺N(R⁹)₄, wherein each R⁹ independently is hydrogen or alkyl, and the nitrogen bearing M⁺ is anionic.

9. The compound of claim 8, wherein p is zero and each of R⁶ and Y, independently, is a straight or branched chain $C_{1-6}$ alkylene group.

10. The compound of claim 9, wherein each of R⁶ and Y, independently, is methylene or ethylene.

11. The compound of claim 1, according to formula III:

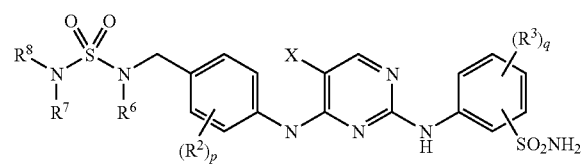

wherein:
p is 0, 1, 2, or 3;
q is 0, 1, 2, or 3;
X is alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl;
each R² independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy, —C(O)N(R⁴)R⁵ or halo;
each R³ independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy or halo;
R⁶ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
R⁷ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
R⁸ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or
R⁷ and R⁸ together, with nitrogen to which they are bound, form a heterocyclyl or substituted heterocyclyl group;
wherein at least one of R⁷ and R⁸ is non-hydrogen; and
each of R⁶, R⁷, and R⁸ optionally are substituted with M⁺, wherein M⁺ is K⁺, Na⁺, Li⁺ or ⁺N(R⁹)₄, wherein each R⁹ independently is hydrogen or alkyl, and the nitrogen bearing M⁺ is anionic.

12. The compound of claim 1, according to formula IV:

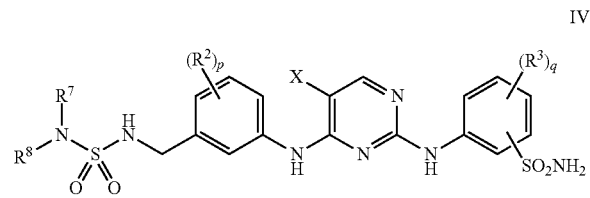

wherein:
p is 0, 1, 2, or 3;
q is 0, 1, 2, or 3;
X is alkyl, substituted alkyl, hydroxy, alkoxy, substituted alkoxy, amino, substituted amino, carboxyl, carboxyl ester, —C(O)N(R⁴)R⁵, cyano, halo, nitro, alkenyl, substituted alkenyl, alkynyl, substituted alkynyl, cycloalkynyl or substituted cycloalkynyl;
each R² independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy, —C(O)N(R⁴)R⁵ or halo;
each R³ independently is alkyl, substituted alkyl, alkoxy, substituted alkoxy, cycloalkyl, substituted cycloalkyl, cycloalkoxy, substituted cycloalkoxy, heterocyclyl, substituted heterocyclyl, heterocyclyloxy, substituted heterocyclyloxy or halo;
R⁶ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
R⁷ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl;
R⁸ is hydrogen, alkyl, substituted alkyl, cycloalkyl, substituted cycloalkyl, heterocyclyl, substituted heterocyclyl, aryl, substituted aryl, heteroaryl, substituted heteroaryl or acyl; or
R⁷ and R⁸ together, with nitrogen to which they are bound, form a heterocyclyl or substituted heterocyclyl group;
wherein at least one of R⁷ and R⁸ is non-hydrogen; and
each of R⁶, R⁷, and R⁸ optionally are substituted with M⁺, wherein M⁺ is K⁺, Na⁺, Li⁺ or ⁺N(R⁹)₄, wherein each R⁹ independently is hydrogen or alkyl, and the nitrogen bearing M⁺ is anionic.

13. A compound which is:

I-1: N2-(3-Aminosulfonylphenyl)-5-chloro-N4-[4-[(N,N-dimethylsulfamoylamino)methyl]phenyl]-2,4-pyrimidinediamine;

I-2: N2-(4-Aminosulfonylphenyl)-5-chloro-N4-[4-[(N,N-dimethylsulfamoylamino)methyl]phenyl]-2,4-pyrimidinediamine;

I-3: N2-(3-Aminosulfonylphenyl)-N4-[4-[(N,N-dimethylsulfamoylamino)methyl]phenyl]-5-methyl-2,4-pyrimidinediamine;

I-4: N2-(4-Aminosulfonylphenyl)-N4-[4-[(N,N-dimethylsulfamoylamino)methyl]phenyl]-5-methyl-2,4-pyrimidinediamine;

I-5: N2-(3-Aminosulfonylphenyl)-5-chloro-N4-[4-[(N-ethylsulfamoylamino)methyl]phenyl]-2,4-pyrimidinediamine;

I-6: N2-(4-Aminosulfonylphenyl)-5-chloro-N4-[4-[(N-ethylsulfamoylamino)methyl]phenyl]-2,4-pyrimidinediamine;

I-7: N2-(3-Aminosulfonylphenyl)-N4-[4-[(N-ethylsulfamoylamino)methyl]phenyl]-5-methyl-2,4-pyrimidinediamine;

I-8: N2-(4-Aminosulfonylphenyl)-N4-[4-[(N-ethylsulfamoylamino)methyl]phenyl]-5-methyl-2,4-pyrimidinediamine;

I-9: N2-(3-Aminosulfonylphenyl)-5-chloro-N4-[3-[(N-ethylsulfamoylamino)methyl]phenyl]-2,4-pyrimidinediamine;

I-10: N2-(4-Aminosulfonylphenyl)-5-chloro-N4-[3-[(N-ethylsulfamoylamino)methyl]phenyl]-2,4-pyrimidinediamine;

I-11: N2-(3-Aminosulfonylphenyl)-N4-[3-[(N-ethylsulfamoylamino)methyl]phenyl]-5-methyl-2,4-pyrimidinediamine;

I-12: N2-(4-Aminosulfonylphenyl)-N4-[3-[(N-ethylsulfamoylamino)methyl]phenyl]-5-methyl-2,4-pyrimidinediamine;

I-13: N2-(3-Aminosulfonylphenyl)-N4-[3-[(N-ethylsulfamoylamino)methyl]phenyl]-5-fluoro-2,4-pyrimidinediamine;

I-14: N2-(4-Aminosulfonylphenyl)-N4-[3-[(N-ethylsulfamoylamino)methyl]phenyl]-5-fluoro-2,4-pyrimidinediamine;

I-15: N2-(3-Aminosulfonylphenyl)-5-chloro-N4-[4-[(N-ethylsulfamoylamino)methyl]-2-methylphenyl]-2,4-pyrimidinediamine;

I-16: N2-(4-Aminosulfonylphenyl)-5-chloro-N4-[4-[(N-ethylsulfamoylamino)methyl]-2-methylphenyl]-2,4-pyrimidinediamine;

I-17: N2-(4-Aminosulfonyl-3,5-dimethylphenyl)-5-chloro-N4-[4-[(N-ethylsulfamoylamino)methyl]-2-methylphenyl]-2,4-pyrimidinediamine;

I-18: N2-(3-Aminosulfonylphenyl)-5-chloro-N4-[4-[(N-cyclopropylsulfamoylamino)methyl]phenyl]-2,4-pyrimidinediamine;

I-19: N2-(4-Aminosulfonylphenyl)-5-chloro-N4-[4-[(N-cyclopropylsulfamoylamino)methyl]phenyl]-2,4-pyrimidinediamine;

I-20: N2-(4-Aminosulfonyl-3,5-dimethylphenyl)-5-chloro-N4-[4-[(N-cyclopropylsulfamoyl-amino)methyl]phenyl]-2,4-pyrimidinediamine;

I-21: N2-(3-Aminosulfonylphenyl)-N4-[4-[(N-cyclopropylsulfamoylamino)methyl]phenyl]-5-methyl-2,4-pyrimidinediamine;

I-22: N2-(4-Aminosulfonylphenyl)-N4-[4-[(N-cyclopropylsulfamoylamino)methyl]phenyl]-5-methyl-2,4-pyrimidinediamine;

I-23: N2-(4-Aminosulfonyl-3,5-dimethylphenyl)-N4-[4-[(N-cyclopropylsulfamoylamino)methyl]phenyl]-5-methyl-2,4-pyrimidinediamine;

I-24: N2-(3-Aminosulfonylphenyl)-5-chloro-N4-[4-[(N-cyclopropylsulfamoylamino)methyl]-2-methylphenyl]-2,4-pyrimidinediamine;

I-25: N2-(4-Aminosulfonylphenyl)-5-chloro-N4-[4-[(N-cyclopropylsulfamoylamino)methyl]-2-methylphenyl]-2,4-pyrimidinediamine;

I-26: N2-(4-Aminosulfonyl-3,5-dimethylphenyl)-5-chloro-N4-[4-[(N-cyclopropylsulfamoyl-amino)methyl]-2-methylphenyl]-2,4-pyrimidinediamine;

I-27: N4-[3-(N-ethyl-N-propionyl)aminosulfonyl-(N-propionyl)aminomethyl]phenyl-5-methyl-N2-(3-propionylaminosulfonyl)phenyl-2,4-pyrimidinediamine;

I-28: N4-[3-(N-ethyl-N-propionyl)aminosulfonyl-(N-propionyl)aminomethyl]phenyl-5-methyl-N2-(3-propionylaminosulfonyl)phenyl-2,4-pyrimidinediamine sodium salt;

I-29: N2-(3-aminosulfonyl-4-methyl)phenyl-N4-(3-ethylaminosulfonylaminomethyl)phenyl-5-methyl-2,4-pyrimidinediamine;

I-30: N2-(3-aminosulfonyl)phenyl-N4-(3-N,N-dimethylaminosulfonylaminomethyl)-5-methyl-2,4-pyrimidinediamine;

I-31: N2-(4-aminosulfonyl)phenyl-N4-(3-N,N-dimethylaminosulfonylaminomethyl)-5-methyl-2,4-pyrimidinediamine;

I-32: N2-(3-aminosulfonyl-4-methyl)phenyl-N4-(3-N,N-dimethylaminosulfonylamino-methyl)-5-methyl-2,4-pyrimidinediamine;

II-1: N2-(3-aminosulfonyl-4-methyl)phenyl-N4-(2-N,N-dimethylaminosulfonyl-1,2,3,4-tetrahydroisoquinolin-7-yl)-5-fluoro-2,4-pyrimidinediamine;

II-2: N2-(3-aminosulfonyl-4-methyl)phenyl-N4-(2-N,N-dimethylaminosulfonyl-2,3-dihydro-1H-isoindol-5-yl)-5-fluoro-2,4-pyrimidinediamine;

II-3: N2-(4-aminosulfonyl)phenyl-N4-(2-N,N-dimethylaminosulfonyl-2,3-dihydro-1H-isoindol-5-yl)-5-methyl-2,4-pyrimidinediamine;

II-4: N2-(3-aminosulfonyl)phenyl-N4-(2-N,N-dimethylaminosulfonyl-2,3-dihydro-1H-isoindol-5-yl)-5-methyl-2,4-pyrimidinediamine; or II-5: N2-(3-aminosulfonyl-4-methyl)phenyl-N4-(2-N,N-dimethylaminosulfonyl-2,3-dihydro-1H-isoindol-5-yl)-5-methyl-2,4-pyrimidinediamine.

14. A pharmaceutical formulation comprising a compound according to claim 1.

* * * * *

UNITED STATES PATENT AND TRADEMARK OFFICE
CERTIFICATE OF CORRECTION

PATENT NO.       : 8,268,851 B2
APPLICATION NO.  : 12/645349
DATED            : September 18, 2012
INVENTOR(S)      : Somasekhar Bhamidipati et al.

Page 1 of 2

It is certified that error appears in the above-identified patent and that said Letters Patent is hereby corrected as shown below:

In the Specification:

Column 5, line 44, "compound of effective" should be --compound effective--; and
Column 5, line 49, "compound of effective" should be --compound effective--.

Column 6, line 59, "N R$^{20}$C(O)cycloalkyl" should be --NR$^{20}$C(O)cycloalkyl--.

Column 7, line 67, "substituted awl," should be --substituted aryl,--.

Column 8, line 15, "substituted awl," should be --substituted aryl,--;
Column 8, line 23, "awl," should be --aryl,--; and
Column 8, line 67, "awl," should be --aryl,--.

Column 10, line 26, "substituted awl," should be --substituted aryl,--.

Column 11, line 11, "refers to ±O-cycloalkenyl." should be --refers to −O-cycloalkenyl.--; and
Column 11, line 20, "substituted awl," should be --substituted aryl,--.

Column 14, line 66, "substituted awl group" should be --substituted aryl group--; and
Column 14, line 67, "substituted awl group" should be --substituted aryl group--.

Column 15, line 5, "(substituted aryl)-substituted awl." should be
--(substituted aryl)-substituted aryl.--.

Column 18, line 9, "substituted heteroaryl and acyl;" should be --substituted heteroaryl and acyl; or--; and
Column 18, line 16, "the ring bearing Y" should be --the ring bearing Y;--.

Column 33, line 66, "formula II, III and W," should be --formula II, III and IV,--.

Signed and Sealed this
First Day of April, 2014

Michelle K. Lee
*Deputy Director of the United States Patent and Trademark Office*

Column 34, line 48, "such as macrophapges" should be --such as macrophages--.

Column 41, line 33, "(Blake et al., 1997, Blood 89:3104-3112)." should be --(Blaire et al., 1997, Blood 89:3104-3112).--.

Column 60, lines 52-54, "I-30: N2-(3-aminosulfonyl)phenyl-N4-(3-N,N-dimethylaminosulfonylaminomethyl) -5-methyl-2,4-pyrimidinediamine;" should be --I-30: N2-(3-aminosulfonyl)phenyl-N4-(3-N,N-dimethylaminosulfonylaminomethyl)phenyl-5-methyl-2,4-pyrimidinediamine;--; and Column 60, lines 62-64, "I-31: N2-(4-aminosulfonyl)phenyl-N4-(3-N,N-dimethylaminosulfonylaminomethyl)-5-methyl-2,4-pyrimidinediamine;" should be --I-31: N2-(4-aminosulfonyl)phenyl-N4-(3-N,N-dimethylaminosulfonylaminomethyl)phenyl-5-methyl-2,4-pyrimidinediamine;--.

Column 61, lines 4-6, "I-32: N2-(3-aminosulfonyl-4-methyl)phenyl-N4-(3-N,N-dimethylaminosulfonylaminomethyl)-5-methyl-2,4-pyrimidinediamine;" should be --I-32: N2-(3-aminosulfonyl-4-methyl)phenyl-N4-(3-N,N-dimethylaminosulfonylaminomethyl)phenyl-5-methyl-2,4-pyrimidinediamine;--.

Column 63, line 49, "the ring bearing Y" should be --the ring bearing Y;--.

In the Claims:

Claim 13, Column 68, lines 26-28, "I-30: N2-(3-aminosulfonyl)phenyl-N4-(3-N,N-dimethylaminosulfonylaminomethyl) -5-methyl-2,4-pyrimidinediamine;" should be --I-30: N2-(3-aminosulfonyl)phenyl-N4-(3-N,N-dimethylaminosulfonylaminomethyl)phenyl-5-methyl-2,4-pyrimidinediamine;--;

Claim 13, Column 68, lines 29-31, "I-31: N2-(4-aminosulfonyl)phenyl-N4-(3-N,N-dimethylaminosulfonylaminomethyl)-5-methyl-2,4-pyrimidinediamine;" should be --I-31: N2-(4-aminosulfonyl)phenyl-N4-(3-N,N-dimethylaminosulfonylaminomethyl)phenyl-5-methyl-2,4-pyrimidinediamine;--; and Claim 13, Column 68, lines 32-34, "I-32: N2-(3-aminosulfonyl-4-methyl)phenyl-N4-(3-N,N-dimethylaminosulfonylaminomethyl)-5-methyl-2,4-pyrimidinediamine;" should be --I-32: N2-(3-aminosulfonyl-4-methyl)phenyl-N4-(3-N,N-dimethylaminosulfonylaminomethyl)phenyl-5-methyl-2,4-pyrimidinediamine;--.